(12) United States Patent
Shin et al.

(10) Patent No.: US 11,045,252 B2
(45) Date of Patent: Jun. 29, 2021

(54) STENT DELIVERY SYSTEM INCLUDING ANODE-TYPE ELECTRICAL CAUTERY TIP

(71) Applicants: TAEWOONG MEDICAL CO., LTD., Gyeonggi-do (KR); Kyong Min Shin, Gyeonggi-do (KR)

(72) Inventors: Kyong Min Shin, Gyeonggi-do (KR); Se Ik Park, Seoul (KR); Kwang Seok Kim, Gyeonggi-do (KR)

(73) Assignees: Kyong Min Shin, Gyeonggi-do (KR); TAEWOONG MEDICAL CO., LTD., Gyeonggi-do (KR)

( * ) Notice: Subject to any disclaimer, the term of this patent is extended or adjusted under 35 U.S.C. 154(b) by 126 days.

(21) Appl. No.: 16/072,520

(22) PCT Filed: Feb. 3, 2017

(86) PCT No.: PCT/KR2017/001172
§ 371 (c)(1),
(2) Date: Jul. 25, 2018

(87) PCT Pub. No.: WO2017/142236
PCT Pub. Date: Aug. 24, 2017

(65) Prior Publication Data
US 2019/0059994 A1 Feb. 28, 2019

(30) Foreign Application Priority Data
Jan. 31, 2017 (KR) ........................ 10-2017-0013801

(51) Int. Cl.
*A61B 18/12* (2006.01)
*A61B 18/14* (2006.01)
(Continued)

(52) U.S. Cl.
CPC ........ *A61B 18/1492* (2013.01); *A61B 18/148* (2013.01); *A61F 2/07* (2013.01);
(Continued)

(58) Field of Classification Search
CPC .............. A61B 18/148; A61B 18/1492; A61B 2018/00083; A61B 2018/00577; A61B 2018/00595; A61B 2018/126
See application file for complete search history.

(56) References Cited

U.S. PATENT DOCUMENTS 6,241,724 B1 * 6/2001 Fleischman ........ A61B 18/1492
600/374
9,452,069 B2 9/2016 Argentine et al.
(Continued)

FOREIGN PATENT DOCUMENTS

CN 1679119 A 10/2005
CN 104125815 A 10/2014
(Continued)

OTHER PUBLICATIONS

International Search Report for corresponding international application No. PCT/KR2017/001172, dated Jun. 2, 2017.

*Primary Examiner* — Daniel W Fowler
(74) *Attorney, Agent, or Firm* — Novick, Kim & Lee, PLLC; Jae Youn Kim; Jihun Kim

(57) ABSTRACT

The present disclosure relates to a stent delivery system. According to the present disclosure, it is possible to minimize the current flow distance in the in-body by integrally conducting two poles to the electrocautery tip, thus enhancing the treatment stability.

26 Claims, 34 Drawing Sheets

(51) Int. Cl.
    *A61F 2/966*      (2013.01)
    *A61F 2/07*        (2013.01)
    *A61F 2/95*        (2013.01)
    A61B 18/00     (2006.01)
    A61F 2/90      (2013.01)

(52) U.S. Cl.
    CPC ............ *A61F 2/95* (2013.01); *A61F 2/966* (2013.01); *A61B 2018/00083* (2013.01); *A61B 2018/00577* (2013.01); *A61B 2018/00595* (2013.01); *A61B 2018/126* (2013.01); *A61F 2/90* (2013.01); *A61F 2/9517* (2020.05); *A61F 2230/0039* (2013.01)

(56) References Cited

U.S. PATENT DOCUMENTS

2001/0056280 A1* 12/2001 Underwood ......... A61B 18/148 606/41
2006/0111704 A1   5/2006 Brenneman et al.
2009/0131798 A1* 5/2009 Minar ..................... A61B 8/12 600/463
2013/0310833 A1   11/2013 Brown Peter et al.
2014/0180389 A1* 6/2014 Shin ........................ A61F 2/966 623/1.12

FOREIGN PATENT DOCUMENTS

| | | |
|---|---|---|
| CN | 104519837 A | 4/2015 |
| EP | 2851024 A1 | 3/2015 |
| JP | 2001-510354 A | 7/2001 |
| JP | 2005511199 A | 4/2005 |
| JP | 2010512858 A | 4/2010 |
| JP | 2010-530260 A | 9/2010 |
| JP | 2015-518741 A | 7/2015 |
| JP | 2015521065 A | 7/2015 |
| KR | 1020070105767 A | 10/2007 |
| KR | 1020100010907 A | 2/2010 |
| KR | 1020130140954 A | 12/2013 |
| KR | 101493766 B1 | 2/2015 |
| WO | 9718768 A1 | 5/1997 |
| WO | 2013052590 A1 | 4/2013 |

* cited by examiner

[FIG. 1]
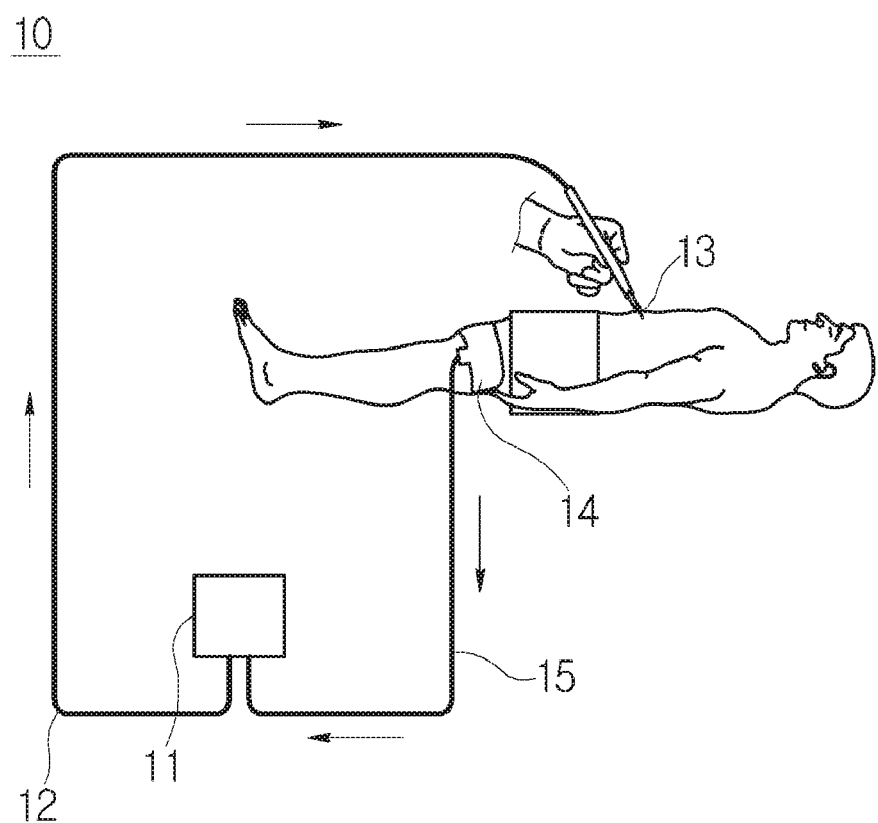

[FIG. 2]
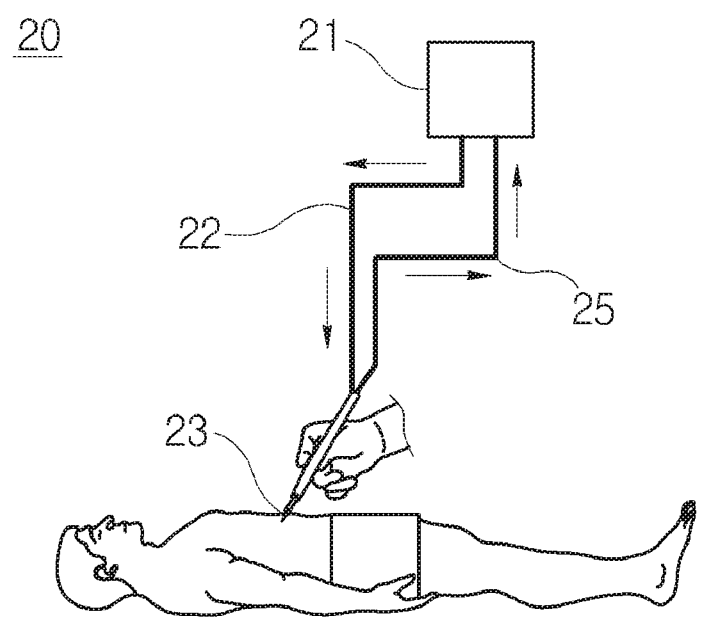

[FIG. 3]
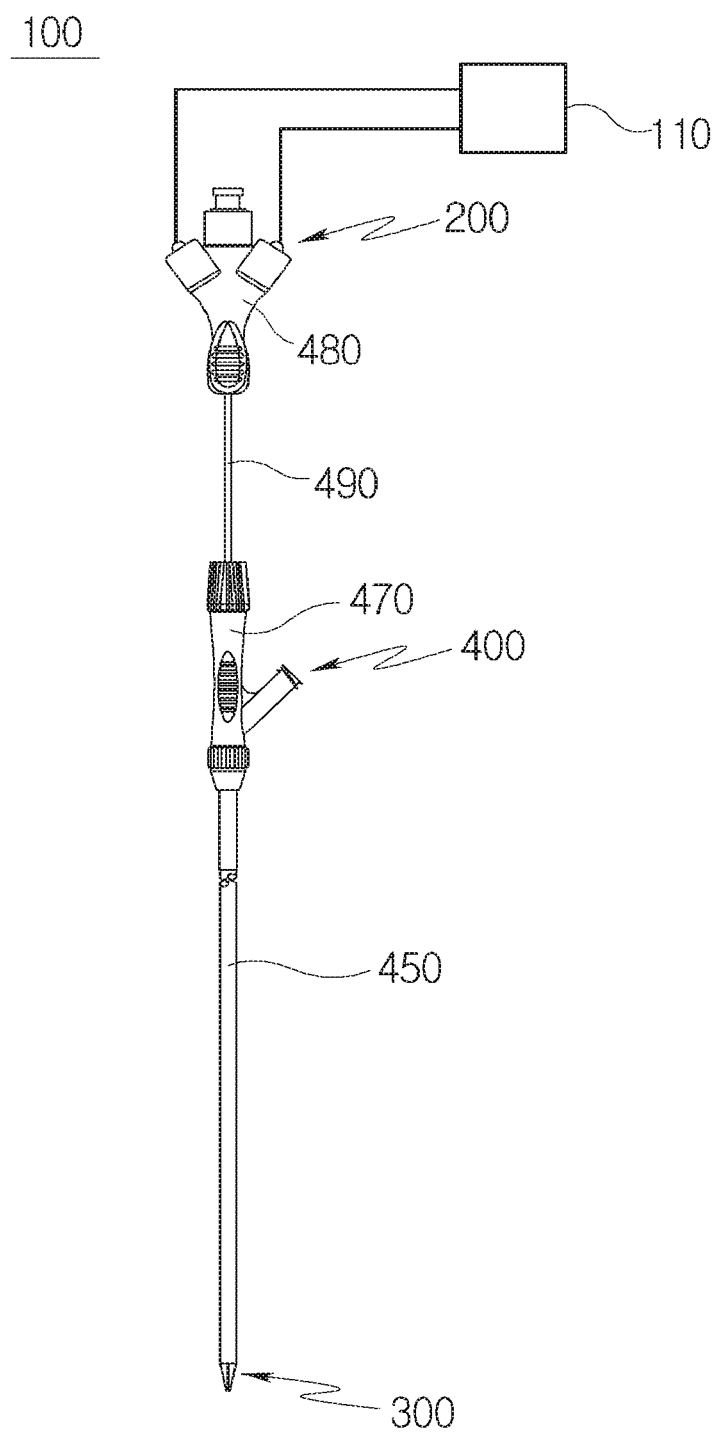

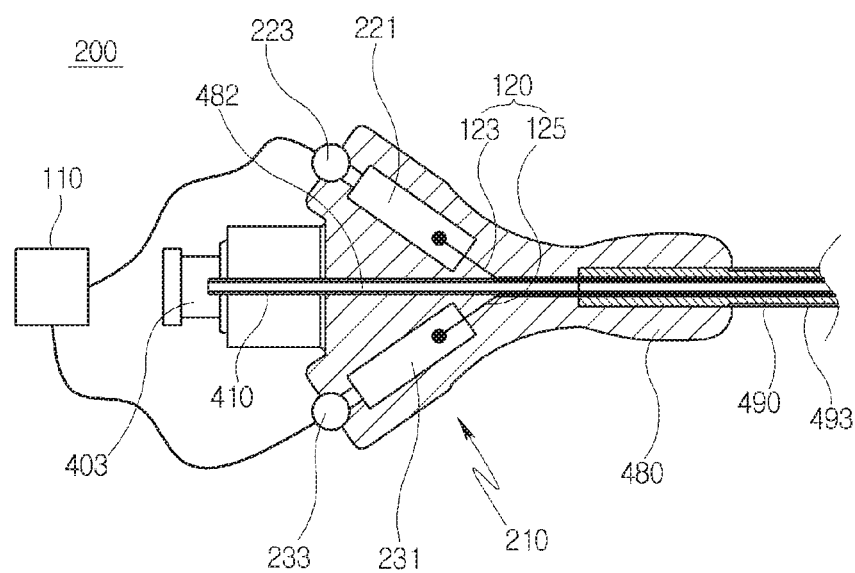
[FIG. 4]

[FIG. 5]
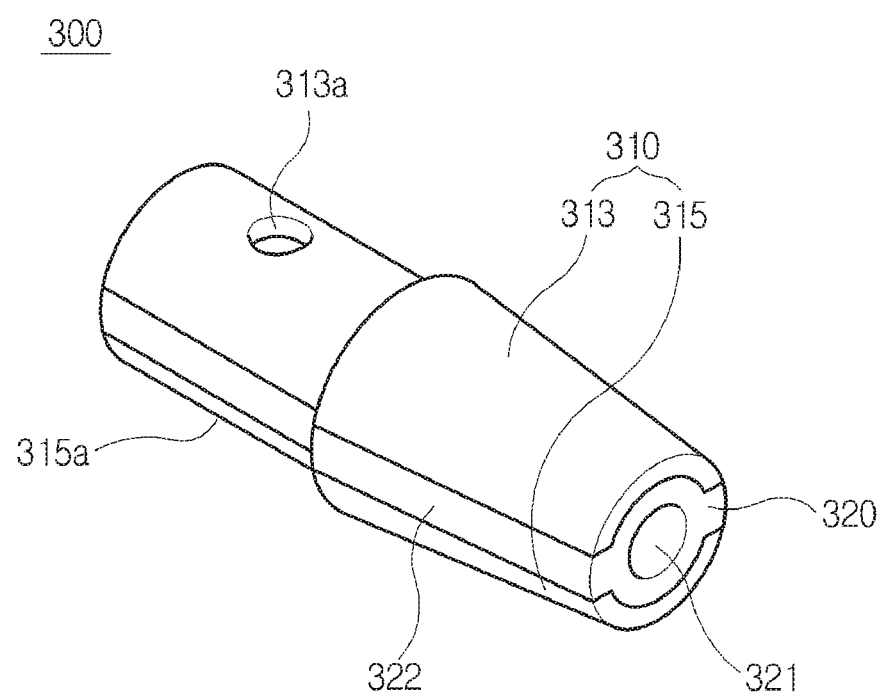

[FIG. 6]
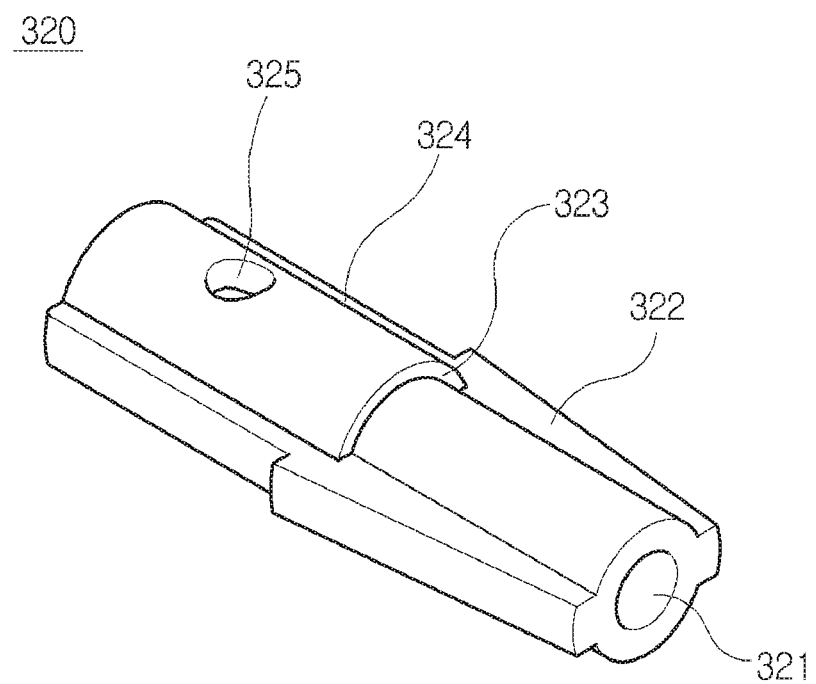

[FIG. 7]
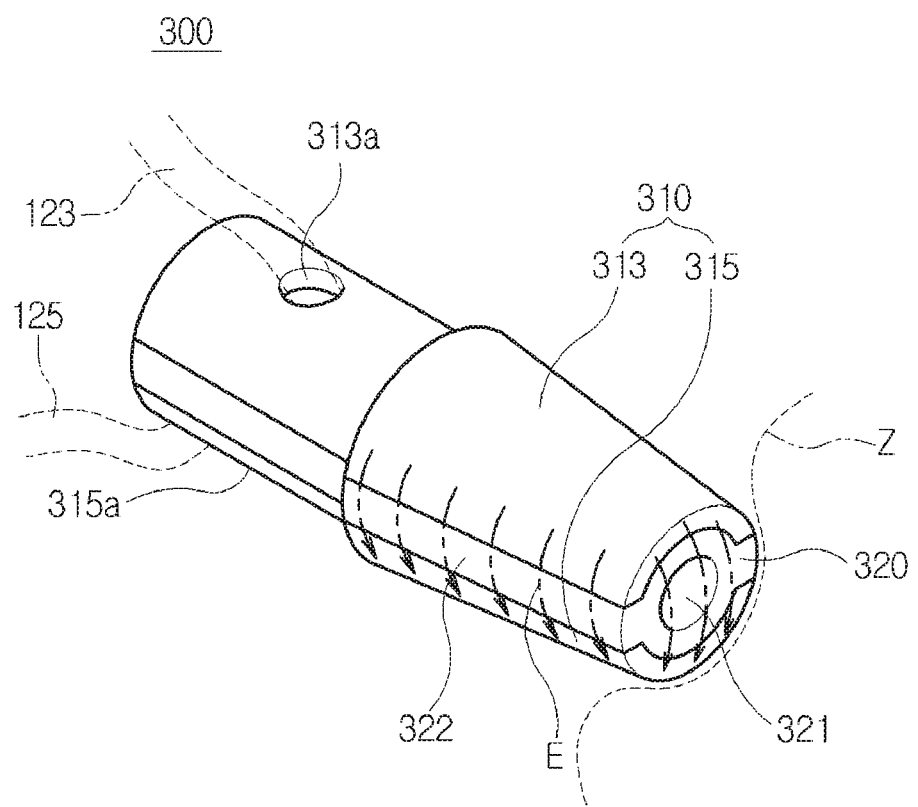

[FIG. 8]
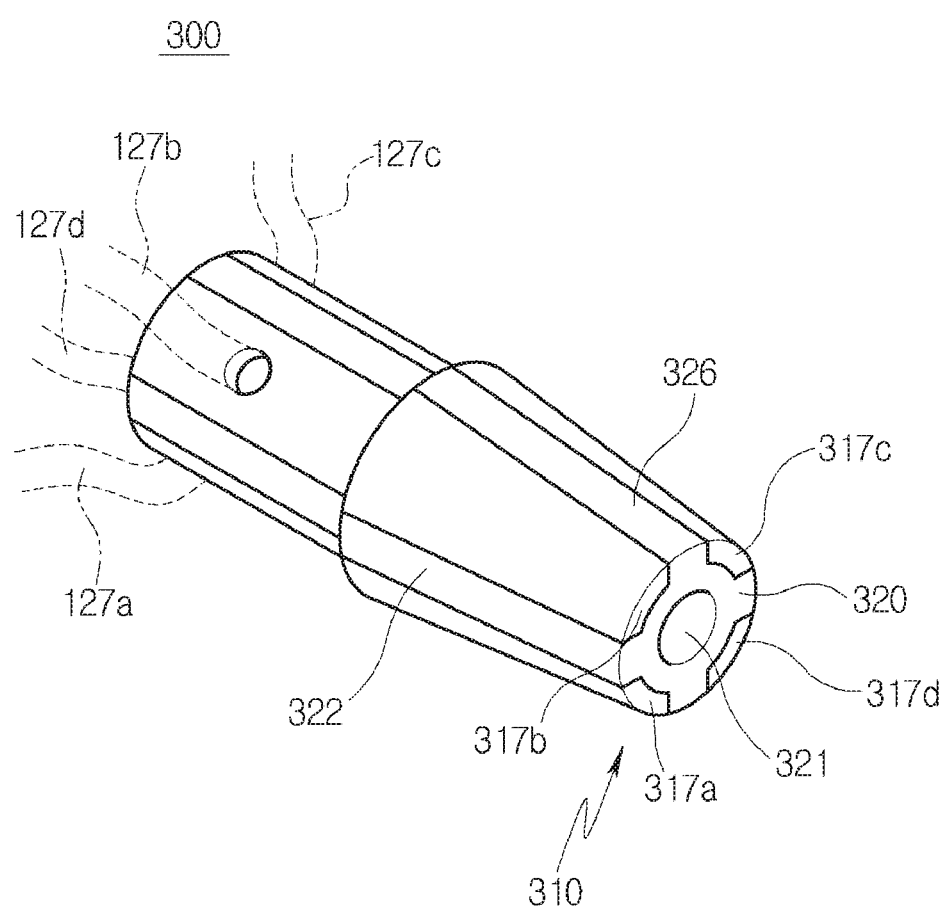

[FIG. 9]
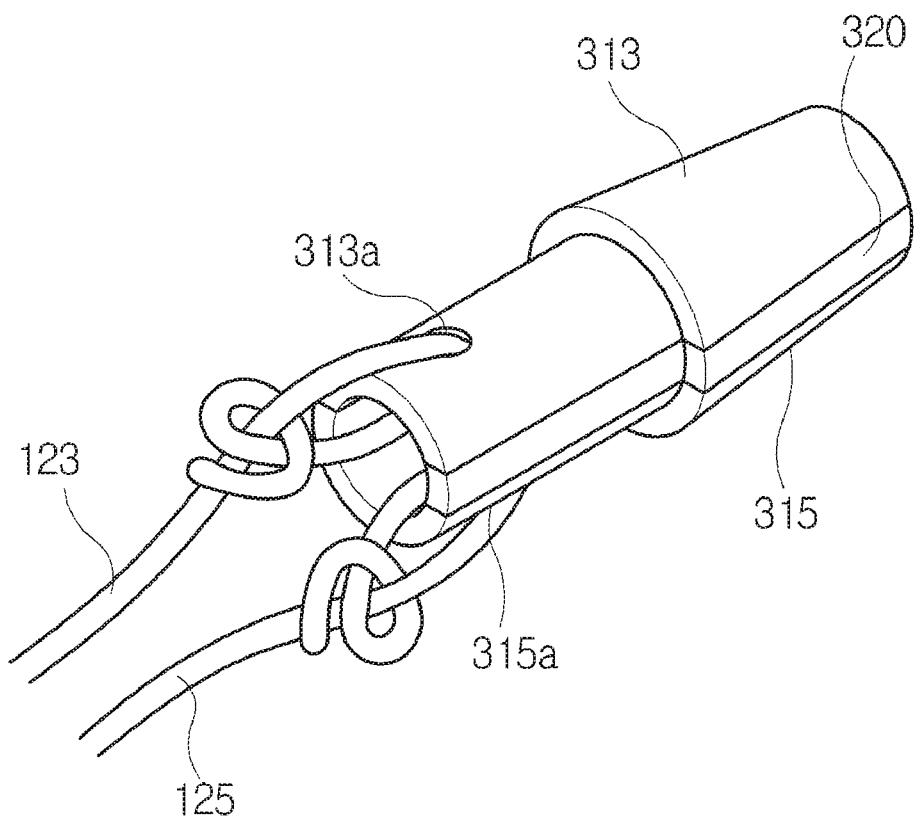

[FIG. 10]
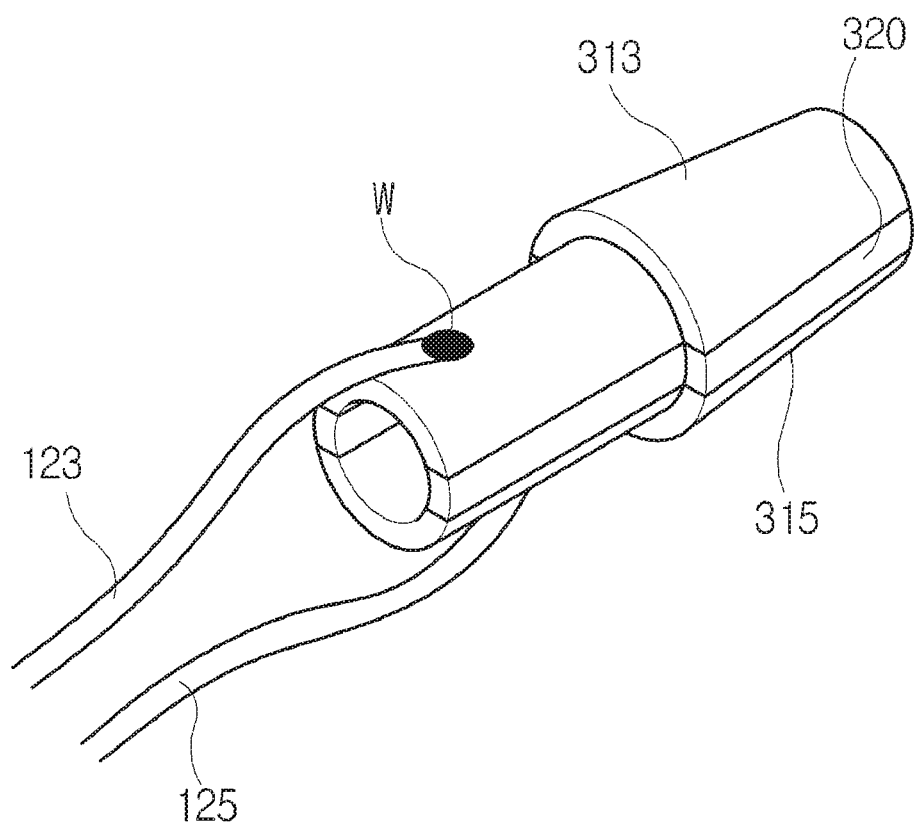

[FIG. 11]
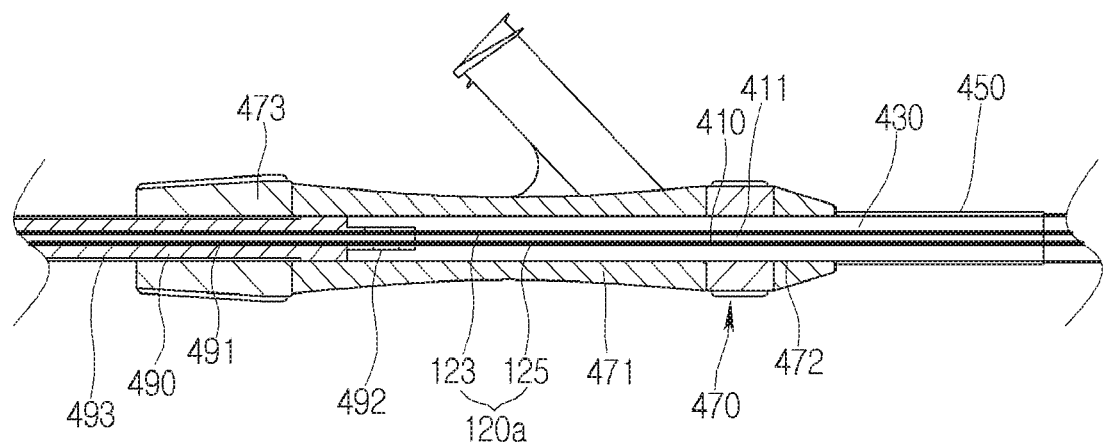

[FIG. 12]
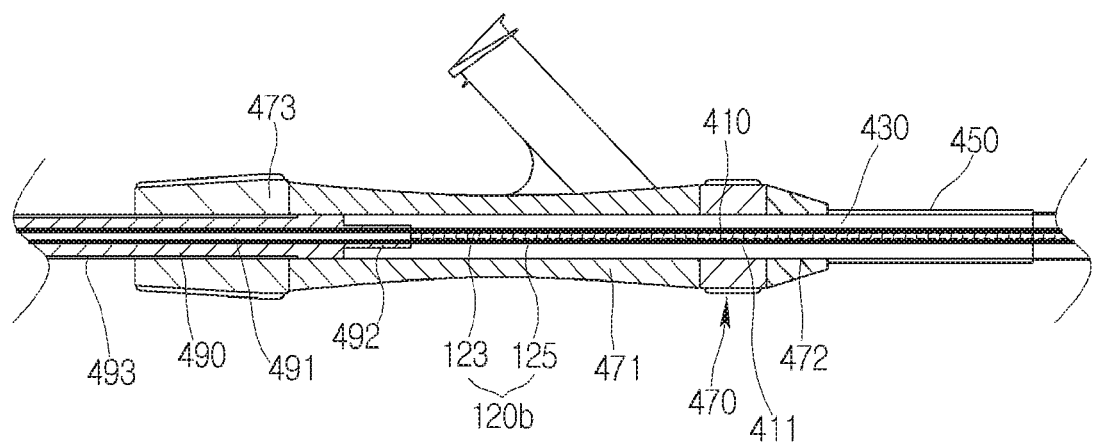

[FIG. 13]
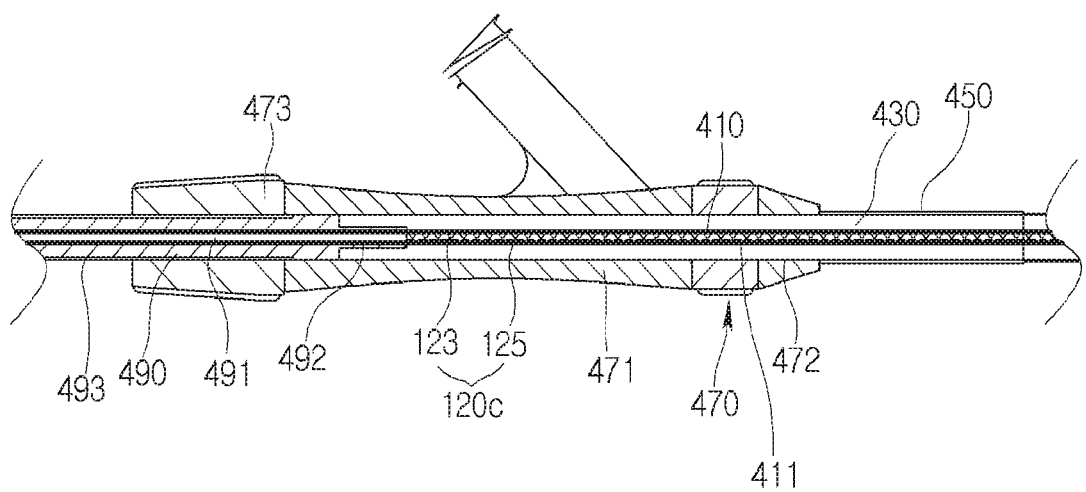

[FIG. 14]
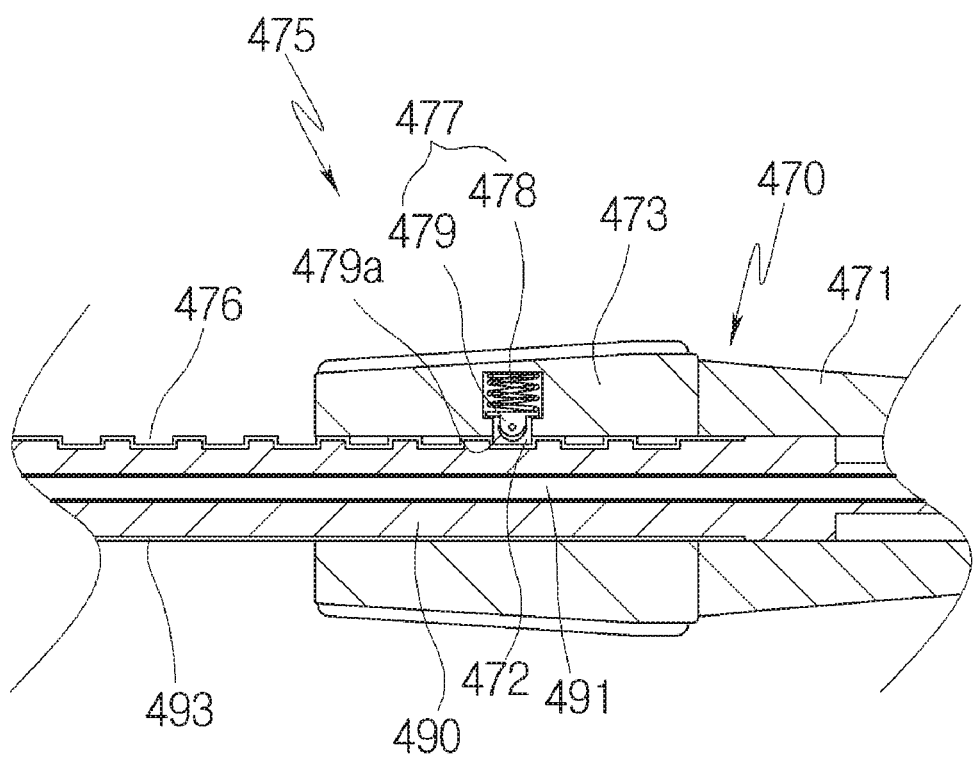

[FIG. 15]
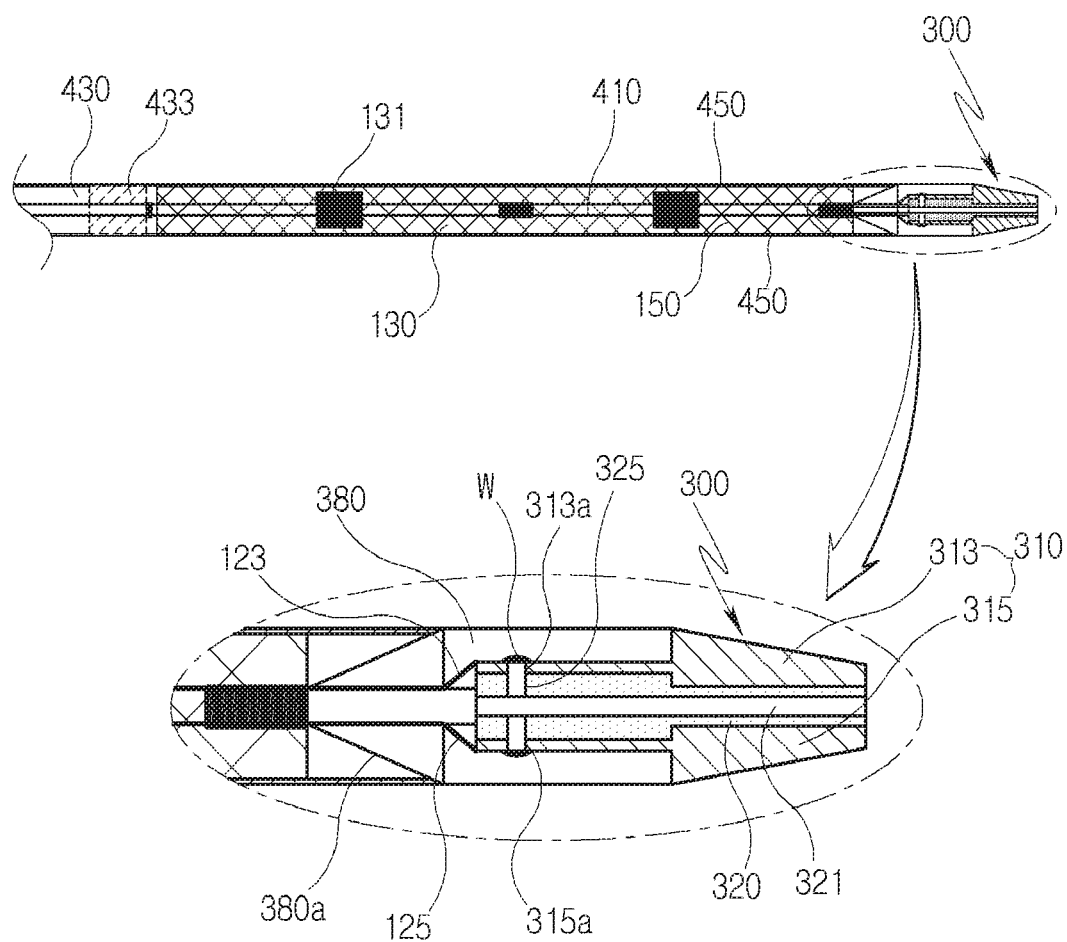

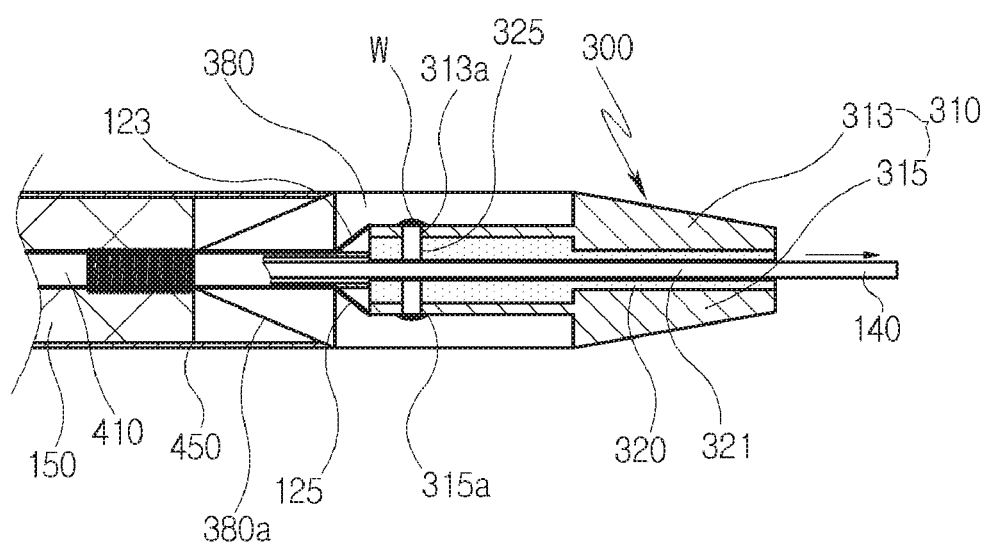
[FIG. 16]

[FIG. 17]
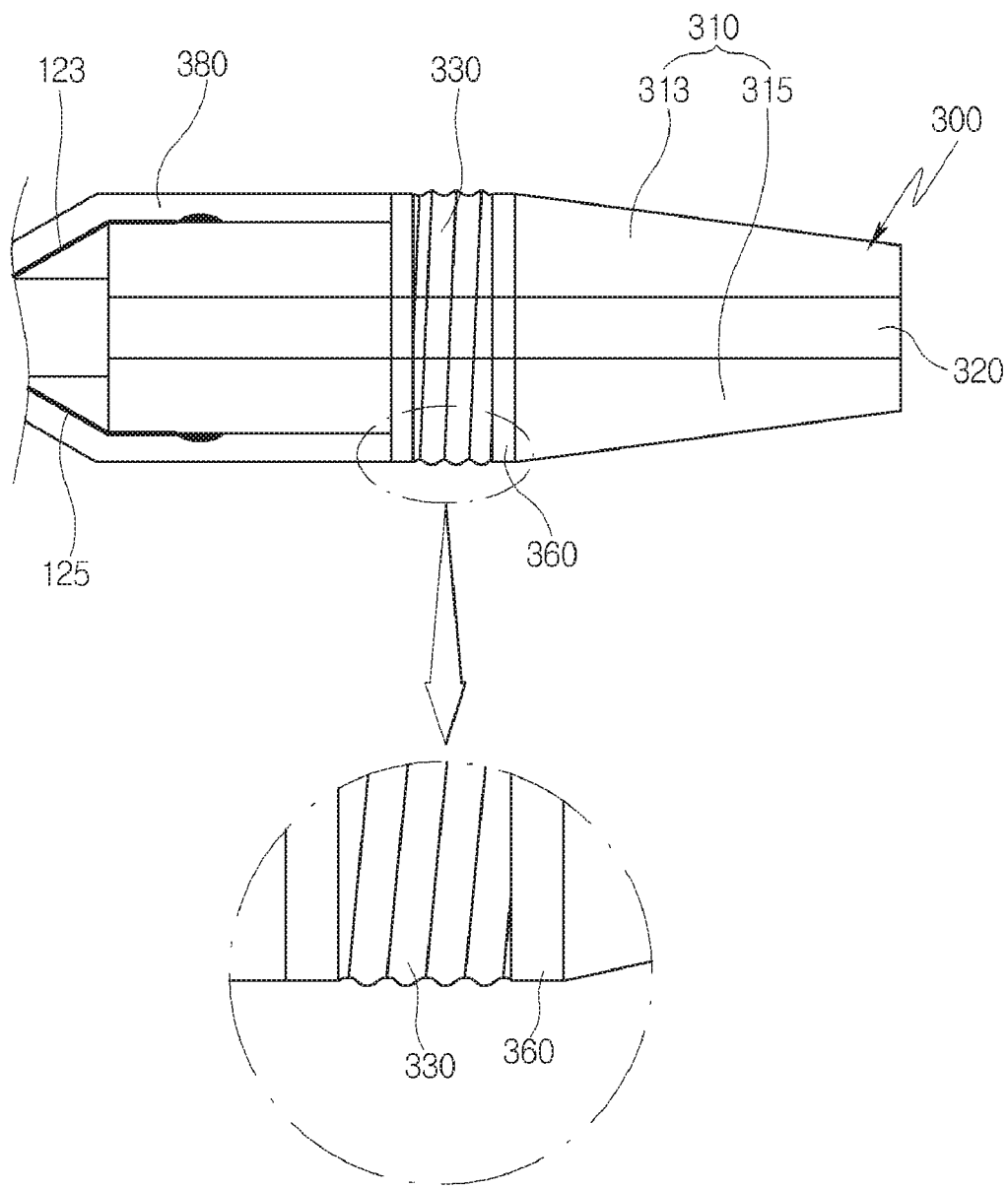

[FIG. 18]
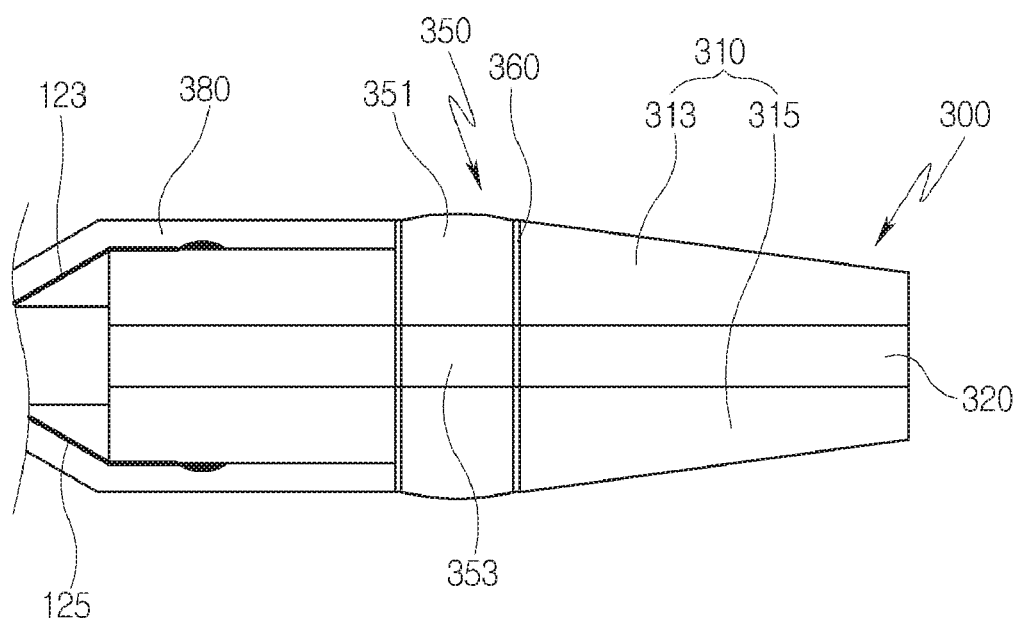

[FIG. 19]
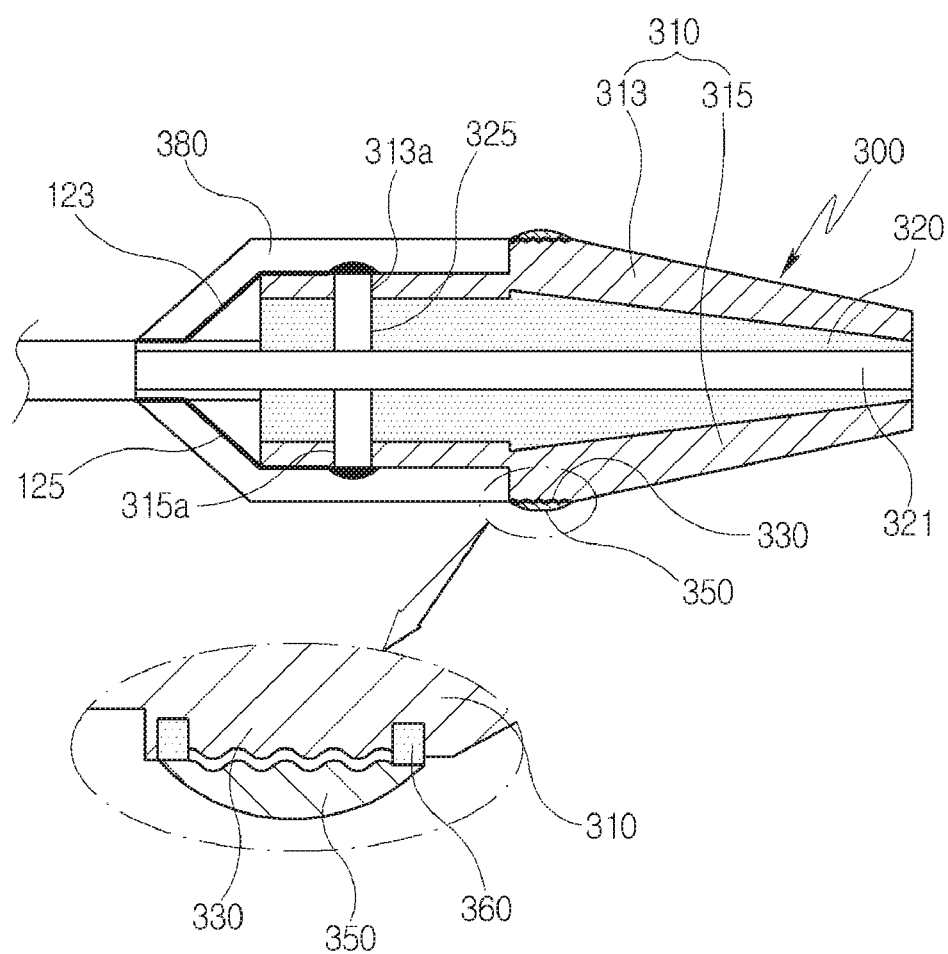

[FIG. 20]
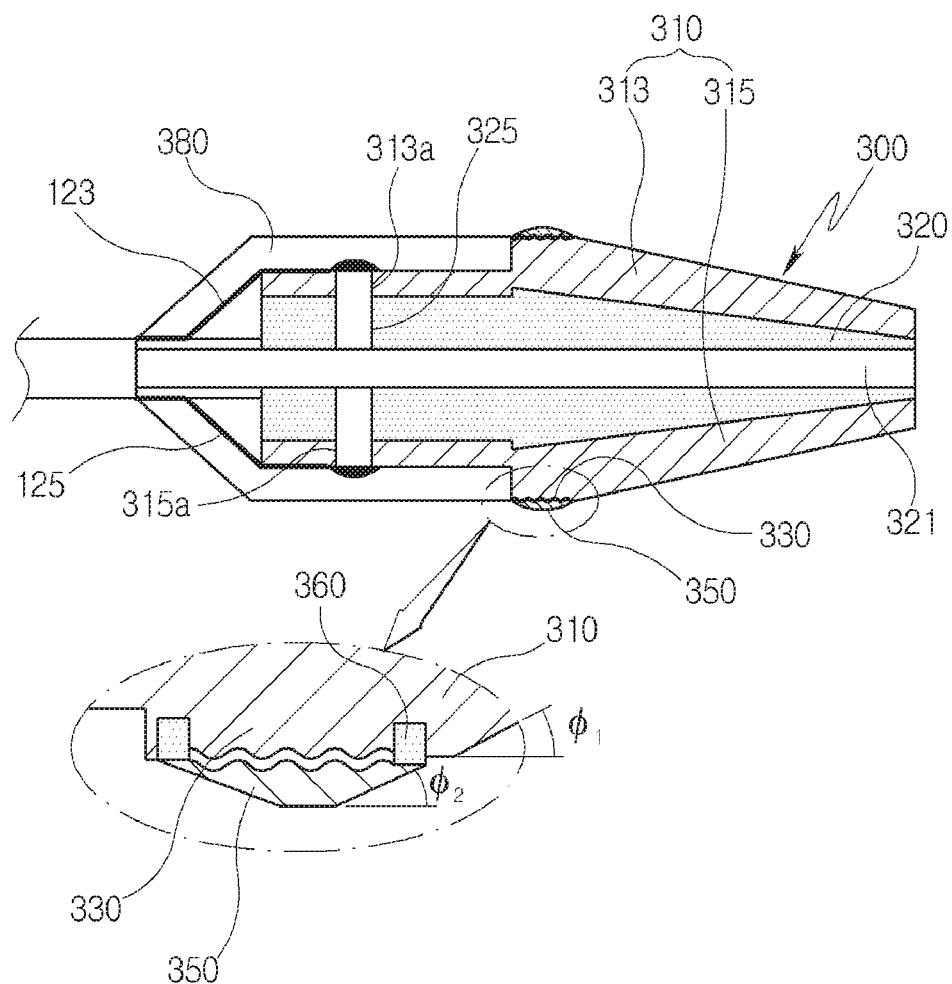

[FIG. 21]
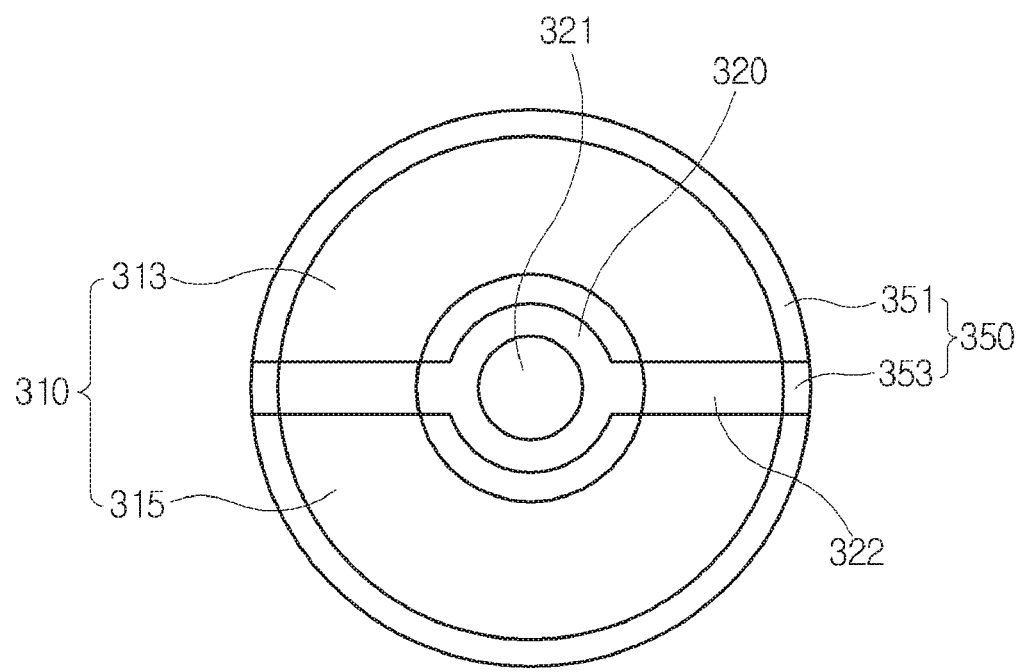

[FIG. 22]
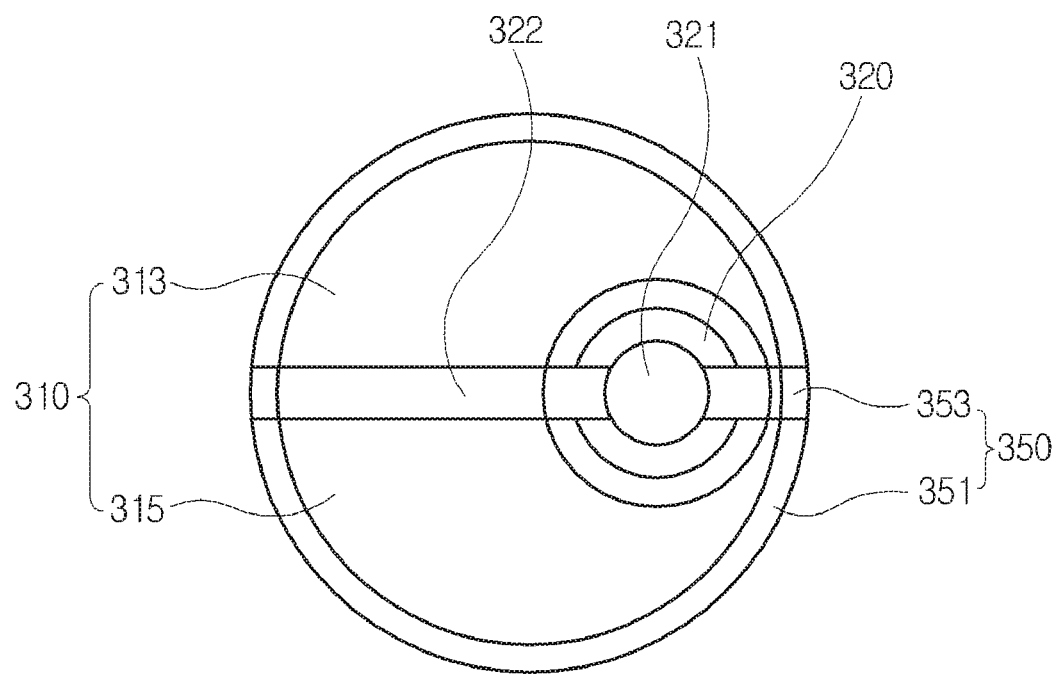

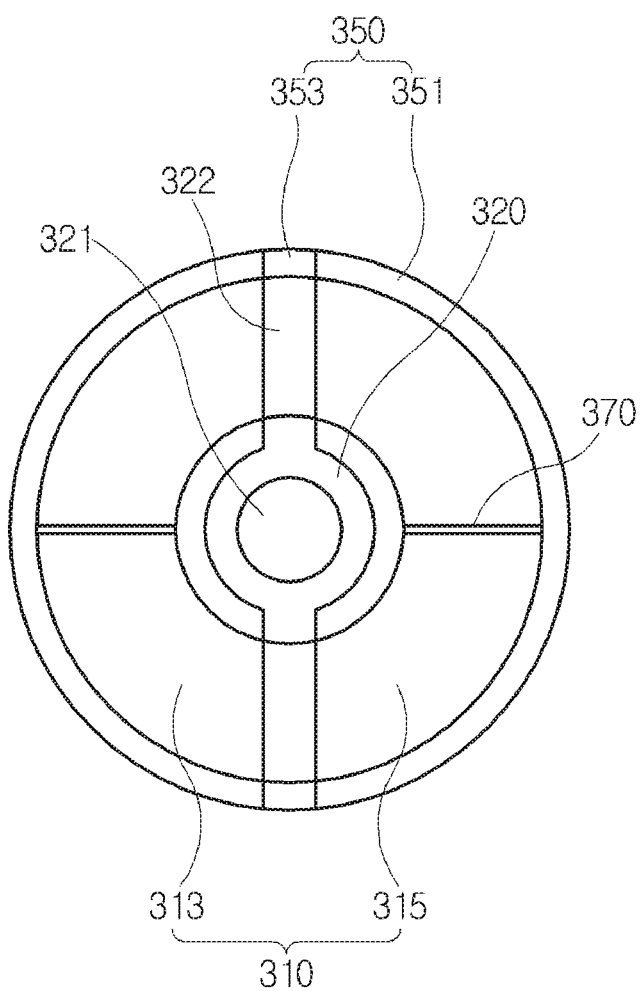
[FIG. 23]

[FIG. 24]
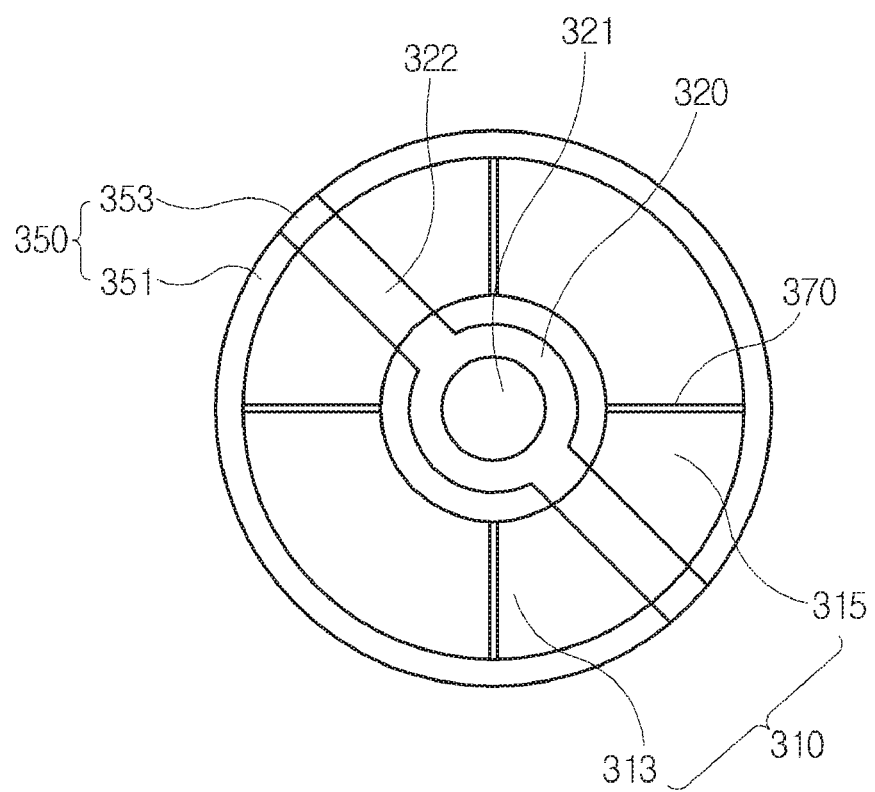

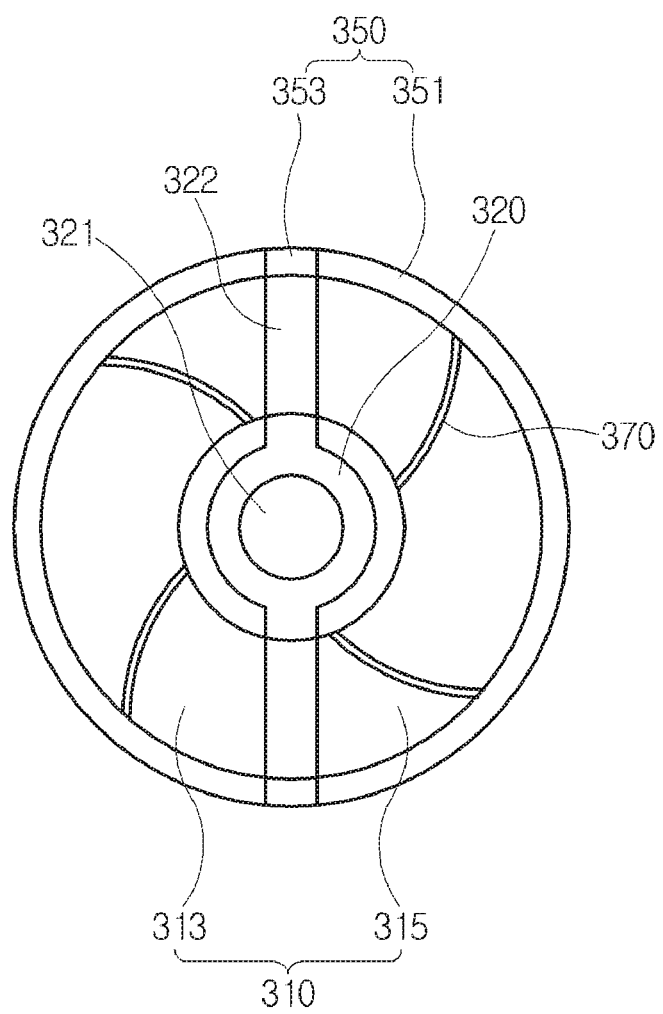
[FIG. 25]

[FIG. 26]
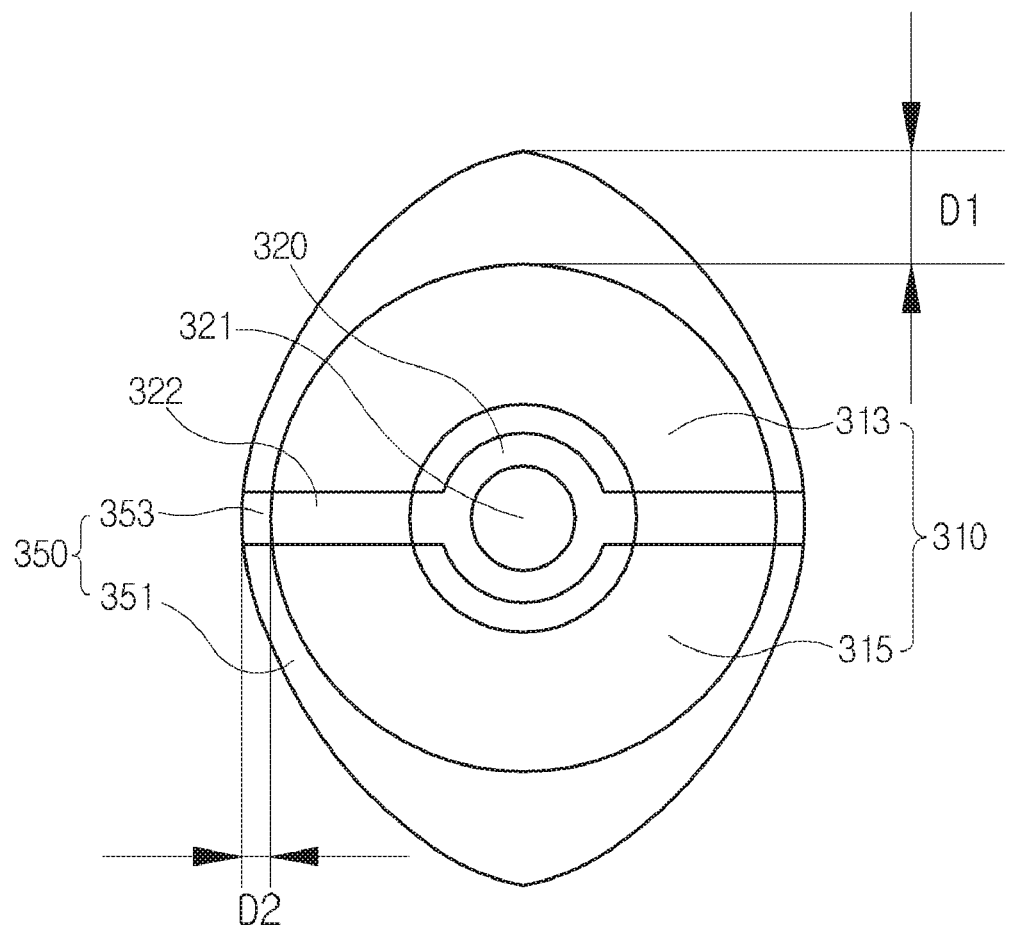

[FIG. 27]
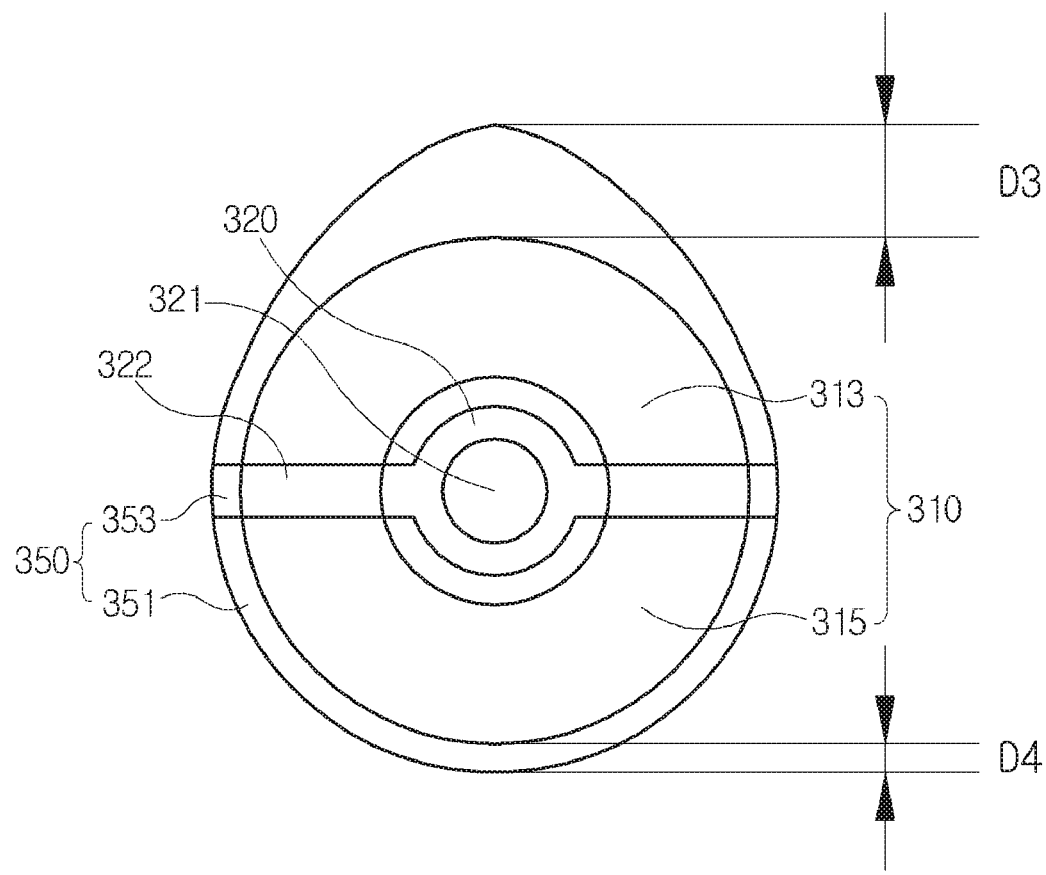

[FIG. 28]
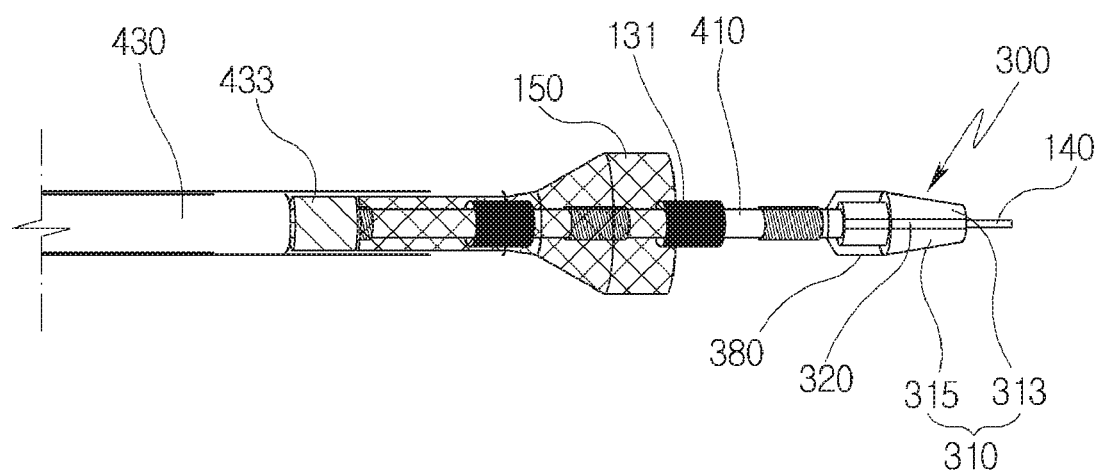

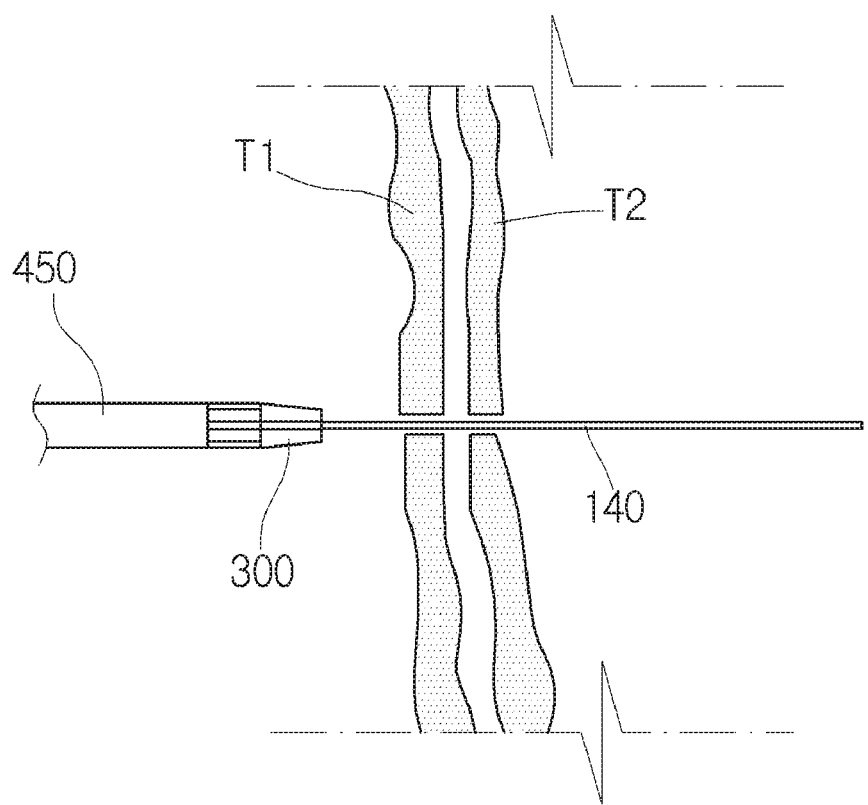
[FIG. 29]

[FIG. 30]
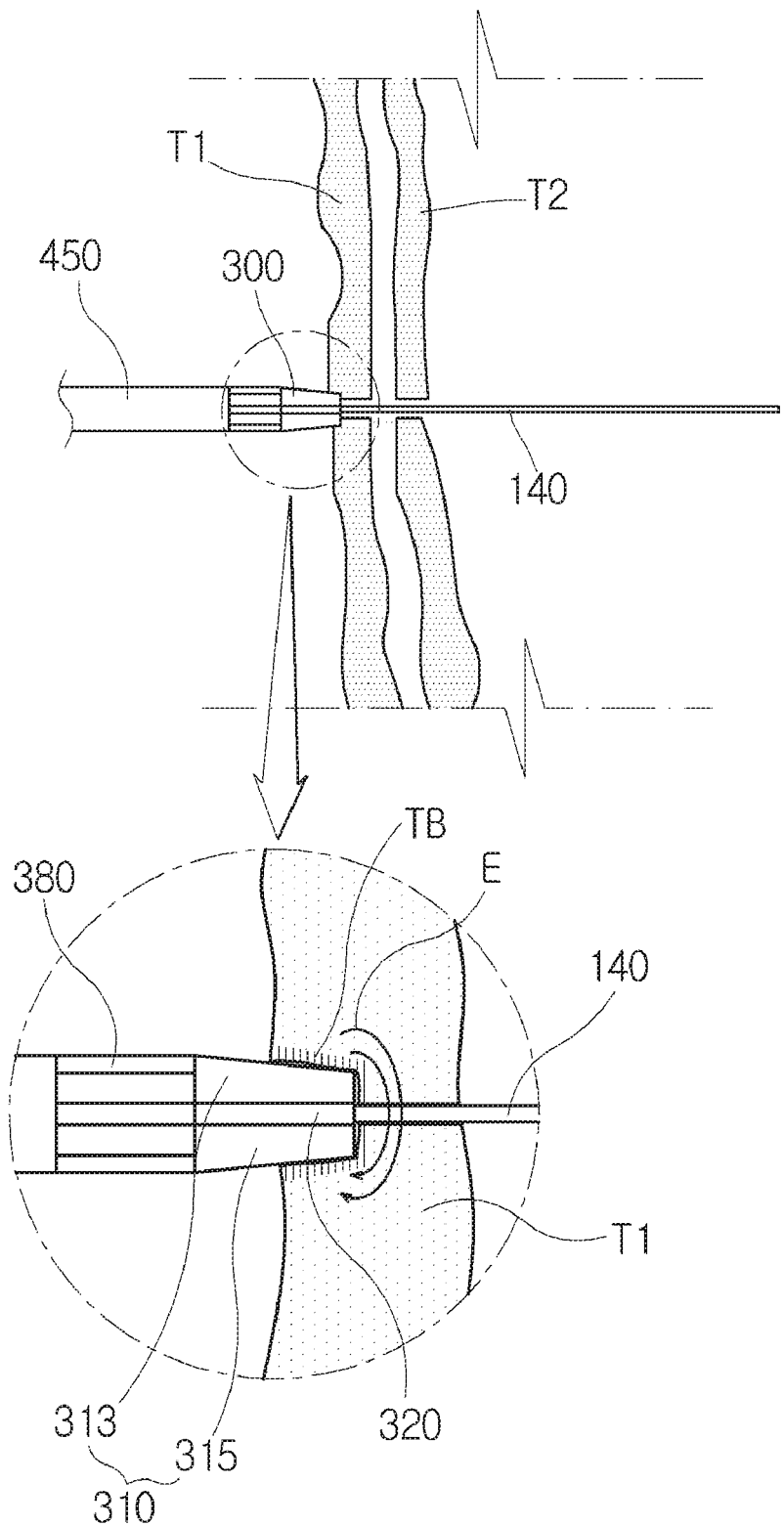

[FIG. 31]
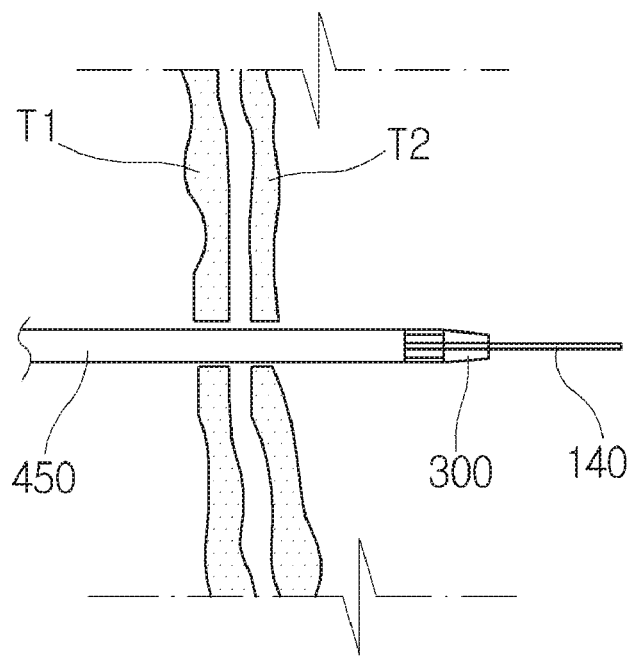

[FIG. 32]
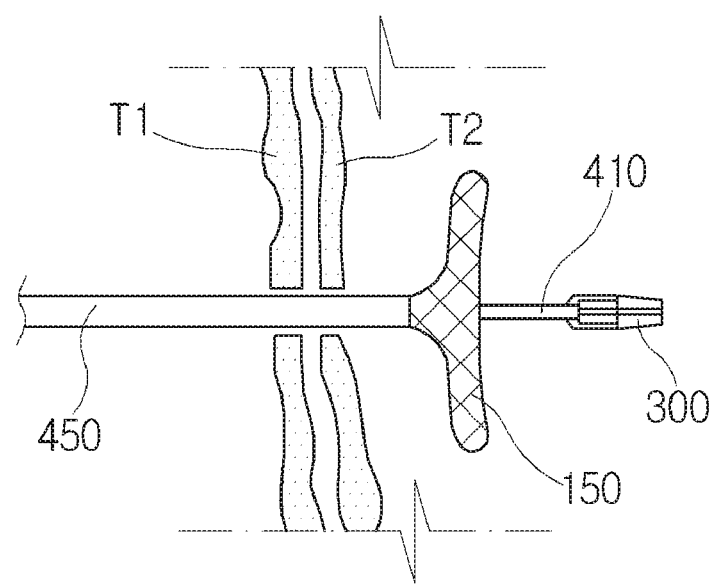

[FIG. 33]
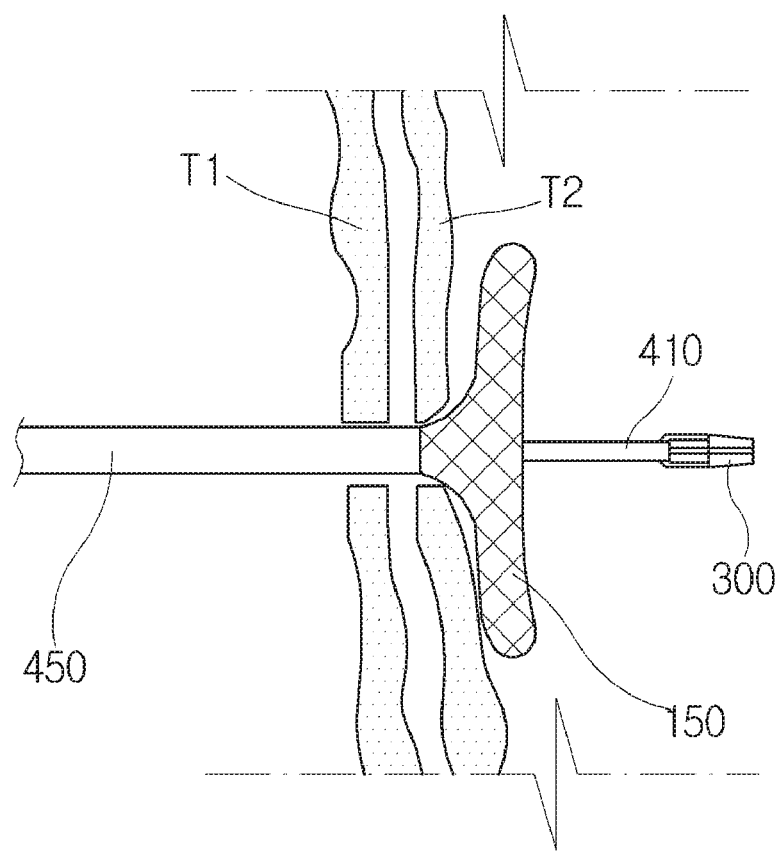

[FIG. 34]
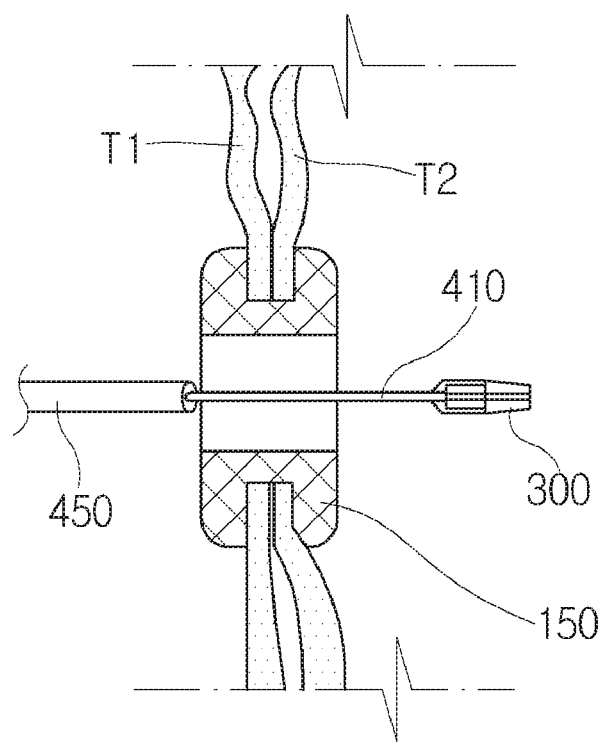

STENT DELIVERY SYSTEM INCLUDING ANODE-TYPE ELECTRICAL CAUTERY TIP

RELATED APPLICATIONS

The present invention is a U.S. National Stage under 35 USC 371 patent application, claiming priority to Serial No. PCT/KR2017/001172, filed on 3 Feb. 2017; which claims priority of KR 10-2016-0017157, filed on 15 Feb. 2016 and KR 10-2017-0013801, filed on 31 Jan. 2017, the entirety of each of which is incorporated herein by reference.

TECHNICAL FIELD

The present disclosure relates to a stent delivery system.

BACKGROUND ART

A stent is an endoprostheses device that is used to secure a circulation passage of blood, body fluid, food, body waste, etc. by inserting it into a blocked body.

The stent is mainly made of a plastic material or a metal material. First, there is a problem in that the plastic material with a thin diameter can be easily inserted, while due to its material property and thin diameter, the self-expansion is collapsed and the stent treatment area is blocked again.

Accordingly, in the medical field, the stent of a metal material is used in many cases. The metal material is expensive but basically has an inherent rigidity, such that even if intermittent muscle contraction or external shock applied in the body tissue of the stent treatment area, etc. occurs, it is temporarily contracted but is self-expanded again, thus efficiently maintaining the function thereof.

Recently, when problems such as occlusion and damage have occurred on the circulation passage of the human body, such as blood vessel, ureter, and bile duct, a non-surgical method is preferred rather than a surgical method as before, and as a part of this trend, the stent treatment is being activated.

A stent delivery system such as a catheter is used to insert the stent into the body tissue area to be treated.

Herein, in simply explaining the stent delivery system, the stent delivery system is basically configured to include an electrocautery tip, an insertion tube, a stent, a handle, a current connector, etc.

The current connector is a part that is connected to an external current source such as an electric treatment instrument to receive a current for heating, and the electrocautery tip is a part that is connected to the current connector by a conduction wire to form a hole by receiving the current to cauterize the body tissue.

Then, the insertion tube is generally made of an insulating material, and the stent is embedded inside the insertion tube, such that the practitioner inserts the insertion tube into the body tissue through a cauterization hole by the operation of the handle, and locates the stent at the area to be treated.

Thereafter, the stent is exposed from the insertion tube through the operation of the handle and the stent is self-expanded, thus solving occlusion, damage, etc. of the treatment area.

Referring to FIG. 1, there are many cases where only mono-pole is located in an electrocautery tip 13 used in many conventional stent delivery systems 10. FIG. 1 illustrates a circuit system provided with the mono-polar electrocautery tip 13, and this is for explaining the operation principle of the mono-polar electrocautery tip 13.

In this case, the treatment method is that the practitioner connects one pole of an external current source 11 with the electrocautery tip 13 using a wire 12, and locates an electrode patch 14 so that the other pole can be conducted to a part of the patient body. Then, the electrode patch 14 is connected to the other pole of the external current source 11 using a wire 15.

The practitioner turns on the power of the external current source 11 to adjust the current magnitude and cauterizes the body tissue. The current flows in the direction of the arrow illustrated in FIG. 1 (or in the opposite direction thereof) and flows in the direction of the electrode patch 14 through the in-body at the end portion of the electrocautery tip 13.

In this time, the current flows in the in-body, such that when a mistake is accidentally made, a patient can receive an electric shock or in a severe case, the patient can suffer body damage, such as tissue burn or tissue necrosis.

In order to alleviate this, it is preferable to make the distance between the electrocautery tip 13 and the electrode patch 14 as close as possible, but there is a physical restriction depending on the location of the body area to be treated.

Accordingly, there is a demand for a structure that can further secure the treatment stability for the patient.

Another problem is that in the conventional stent delivery system, the insertion tube is made of an insulating material, such that when the practitioner such as a doctor or a nurse applies the shock due to their erroneous usage, the phenomenon that is easily bent or broken occurs. In the severe case, a problem can also occur that it is broken due to external damage.

When the problems occur during the actual treatment, it can result in a fatal medical accident for the person to be treated, such as a patient.

The insertion tube is inserted into the human body, such that some flexibility thereof should be ensured, and in addition, it is a part touching the human body, such that the insulation property should be electrically maintained. Accordingly, in the stent treatment technology field, there is a demand for a tube with the enhanced durability in order not to be easily damaged even by the carelessness of the practitioner, such as a doctor or a nurse, while maintaining the basic characteristics of the above-mentioned insertion tube. Of course, the location of the conduction wire connected to the electrocautery tip should be also considered adequately.

In addition, there is a problem in that most of stent delivery systems currently used have a fixed size of the electrocautery tip, such that the size of the cauterization hole cannot be adjusted depending upon the treatment environment in the body tissue of the person to be treated. This results in the limitation that cannot adequately cope with a change in the variable treatment environment.

Accordingly, in order to provide more advanced treatment environment, there is a demand for a treatment device that can variably adjust the cauterization hole in the body tissue in order to deliver various types of stents required in the treatment area of the body tissue.

DISCLOSURE

Technical Problem

The present disclosure is intended to solve the problems of the related art as described above, and an object of the present disclosure is to a stent delivery system, which can minimize the current flow distance in the in-body by integrally conducting two poles to the electrocautery tip, thus enhancing the treatment stability.

Technical Solution

The present disclosure for achieving the objects relates to a stent delivery system, and can include a connector portion having a plurality of connection connectors, at least any one of which is connected to an external current source with a different pole; an electrocautery tip integrally having a plurality of electrode bodies that are connected by a plurality of electrode lines corresponded to the plurality of connection connectors and at least one of which is conducted with a different pole; a delivery portion having one side connected to the electrocautery tip, having the other side connected to the connector portion, and having the electrode line connecting the electrocautery tip and the connector portion located therein; and a stent space portion located adjacent to the electrocautery tip inside the delivery portion.

In addition, in the embodiment of the present disclosure, the electrocautery tip can include a tip insulating member having a tip guide hole formed therein; a first electrode body located on one side surface of the tip insulating member and forming any one pole; and a second electrode body located on the other side surface of the tip insulating member and forming the other one pole.

In addition, in the embodiment of the present disclosure, the plurality of connection connectors can be divided into a first connection connector and a second connection connector, and the plurality of electrode lines can be divided into a first electrode line connecting the first electrode body with the first connection connector, and a second electrode line connecting the second electrode body with the second connection connector.

In addition, in the embodiment of the present disclosure, one side portions of the first electrode body and the second electrode body can be tapered in the direction facing each other.

In addition, in the embodiment of the present disclosure, the delivery portion can include a first internal tube having the electrode line connected to the electrocautery tip located thereon, and having an inner hole formed at the internal central side thereof; a second internal tube located to surround a part of the outside circumference of the first internal tube, and provided to be connected with the first internal tube to be integrally moved; and an external tube located to surround the second internal tube.

In addition, in the embodiment of the present disclosure, the first internal tube can be an insulation coating agent, and the first electrode line and the second electrode line can be individually insulation-coated and can be located in the straight-line shape along the longitudinal direction of the first internal tube.

In addition, in the embodiment of the present disclosure, the first internal tube can be an insulation coating agent, and the first electrode line and the second electrode line can be individually insulation-coated and can be located to be wound in the spiral direction along the circumference of the first internal tube.

In addition, in the embodiment of the present disclosure, the first internal tube can be an insulation coating agent, and the first electrode line and the second electrode line can be individually insulation-coated and can be located in the woven shape along the circumference of the first internal tube.

In addition, in the embodiment of the present disclosure, the delivery portion can further include a first handle portion connected to the external tube, and a second handle portion connected to the second internal tube by a movable bar; and the connector portion can be located on the second handle portion, and the first internal tube can be located to penetrate the movable bar and the second handle portion.

In addition, in the embodiment of the present disclosure, the electrocautery tip can further include a coupling portion formed on a part of the outside circumference of the electrode body; and a variable ring connected to the coupling portion in order to change the size of the electrode body.

In addition, in the embodiment of the present disclosure, a part of the outside of the variable ring can be tapered in the same direction as the first electrode body and the second electrode body.

In addition, in the embodiment of the present disclosure, a part of the outside of the variable ring can be tapered at an angle smaller than the first electrode body and the second electrode body.

In addition, in the embodiment of the present disclosure, the outside circumference of the variable ring can be processed to be rounded.

In addition, in the embodiment of the present disclosure, a part of the variable ring can have a different thickness.

In addition, in the embodiment of the present disclosure, the electrocautery tip can further include an adhesion pad located on at least any one side of the coupling portion in order to prevent the gap between the inside circumference of the variable ring and the outside circumferences of the electrode body and the tip insulating member.

In addition, in the embodiment of the present disclosure, the electrocautery tip can further include an electrocautery protrusion formed on the outside surface of the electrode body.

In addition, in the embodiment of the present disclosure, the electrocautery protrusion can be located in plural on the outside circumference of the electrode body at predetermined intervals.

In addition, in the embodiment of the present disclosure, the electrocautery protrusion can be a straight-line shape.

In addition, in the embodiment of the present disclosure, the electrocautery protrusion can be a curve shape.

In addition, the embodiment of the present disclosure can further include a guide wire located on an inner hole of the first internal tube and a tip guide hole of the tip insulating member and for guiding the movement direction of the electrocautery tip.

In addition, in the embodiment of the present disclosure, the delivery portion can further include a movement adjustment unit for adjusting the movement of a movable bar in the stepwise manner; and the delivery portion can include an uneven portion formed along the longitudinal direction of the movable bar, and a fixing portion coupled to the uneven portion and located inside the first handle portion in order to fix the movement of the movable bar in the stepwise manner.

In addition, in the embodiment of the present disclosure, the fixing portion can include an elastic body located inside the first handle portion; and a fixing block having one side tightly contacted to the elastic body, and having the other side located to be protruded to the first inner hole.

In addition, in the embodiment of the present disclosure, the fixing portion can further include a rolling wheel rotatably located on the fixing block.

In addition, in the embodiment of the present disclosure, the tip guide hole can be eccentrically located inside the tip insulating member.

Advantageous Effects

According to the present disclosure, it is possible to minimize the current flow distance for tissue cauterization in the patient's body compared to the related art by integrally conducting two poles to the electrocautery tip, thus preventing burn or electric shock that can occur to the patient. As a result, the treatment stability is further enhanced.

In addition, it can be expected to enhance the rigidity of the tube by integrating the conduction wire and the tube located on the innermost thereof. In this time, the shape that the conduction wire is located to be spirally wound in plural and the shape that is located to be connected by the repetitive woven structure further enhance the rigidity for the entire tube.

In addition, it is possible to change the size, that is, a diameter of the electrocautery tip, thus appropriately adjusting the size that forms a hole in the human body depending upon the size of the treatment area, the cross-sectional size of the tube, and the degree of expansion and contraction of the stent.

In addition, it can be additionally expected to minimize the incision area of the body tissue through the structure, which provides the electrocautery protrusion pattern to the electrocautery tip and applies the current only to the pattern area.

DESCRIPTION OF DRAWINGS

FIG. 1 is a diagram illustrating an operation method of the electrocautery of the body tissue using the conventional mono-polar electrocautery tip.

FIG. 2 is a diagram illustrating an operation method of the electrocautery of the body tissue using a anode-type electrical cautery tip.

FIG. 3 is an appearance diagram of a stent delivery system in accordance with the present disclosure.

FIG. 4 is a side cross-sectional diagram illustrating a connector portion and a second handle portion in the disclosure illustrated in FIG. 3.

FIG. 5 is a perspective diagram illustrating a structure of a anode-type electrical cautery tip in accordance with the present disclosure.

FIG. 6 is a perspective diagram illustrating a tip insulating member in the disclosure illustrated in FIG. 5.

FIG. 7 is a diagram illustrating a current flow in the anode-type electrical cautery tip.

FIG. 8 is a perspective diagram illustrating anther structure of the anode-type electrical cautery tip in accordance with the present disclosure.

FIG. 9 is a diagram illustrating one shape that connects an electrode line to the electrocautery tip.

FIG. 10 is a diagram illustrating another shape that connects the electrode line to the electrocautery tip.

FIG. 11 is a side cross-sectional diagram illustrating a straight-line location structure of a delivery portion and the electrode line in accordance with the present disclosure.

FIG. 12 is a side cross-sectional diagram illustrating a spiral location structure of the delivery portion and the electrode line in accordance with the present disclosure.

FIG. 13 is a side cross-sectional diagram illustrating a woven location structure of the delivery portion and the electrode line in accordance with the present disclosure.

FIG. 14 is a side cross-sectional diagram illustrating a structure of a movement adjustment unit in accordance with the present disclosure.

FIG. 15 is a side cross-sectional diagram illustrating the electrocautery tip and the stent space portion in accordance with the present disclosure.

FIG. 16 is a side cross-sectional diagram illustrating the state that is induced by a guide wire in the disclosure illustrated in FIG. 15.

FIG. 17 is a diagram illustrating a structure of a coupling portion formed on the electrocautery tip in accordance with the present disclosure.

FIG. 18 is a diagram illustrating the state in which a variable ring is mounted in the disclosure illustrated in FIG. 17.

FIG. 19 is a side cross-sectional diagram illustrating one shape of the variable ring.

FIG. 20 is a side cross-sectional diagram illustrating another shape of the variable ring.

FIGS. 21 to 25 are diagrams illustrating various shapes of an electrocautery protrusion in accordance with the present disclosure.

FIGS. 26 and 27 are diagrams illustrating various shapes of the variable ring having different lengths.

FIG. 28 is a diagram illustrating the state in which the stent is expanded.

FIGS. 29 to 34 are diagrams illustrating operation procedures that deliver the stent into the body tissue in accordance with the present disclosure.

BEST MODE

Hereinafter, preferred embodiments of a stent delivery system in accordance with the present disclosure will be described in detail with reference to the accompanying drawings.

FIG. 2 is a diagram illustrating an operation method of the electrocautery of the body tissue using a anode-type electrical cautery tip, FIG. 3 is an appearance diagram of a stent delivery system in accordance with the present disclosure, and FIG. 4 is a side cross-sectional diagram illustrating a connector portion and a second handle portion in the disclosure illustrated in FIG. 3. Then, FIG. 5 is a perspective diagram illustrating a structure of a anode-type electrical cautery tip in accordance with the present disclosure, FIG. 6 is a perspective diagram illustrating a tip insulating member in the disclosure illustrated in FIG. 5, and FIG. 7 is a diagram illustrating a current flow in the anode-type electrical cautery tip. Then, FIG. 8 is a perspective diagram illustrating anther structure of the anode-type electrical cautery tip in accordance with the present disclosure, FIG. 9 is a diagram illustrating one shape that connects an electrode line to the electrocautery tip, and FIG. 10 is a diagram illustrating another shape that connects the electrode line to the electrocautery tip. Then, FIG. 11 is a side cross-sectional diagram illustrating a straight-line location structure of a delivery portion and the electrode line in accordance with the present disclosure, FIG. 12 is a side cross-sectional diagram illustrating a spiral location structure of the delivery portion and the electrode line in accordance with the present disclosure, and FIG. 13 is a side cross-sectional diagram illustrating a woven location structure of the delivery portion and the electrode line in accordance with the present disclosure. Then, FIG. 14 is a side cross-sectional diagram illustrating a structure of a movement adjustment unit in accordance with the present disclosure, FIG. 15 is a side cross-sectional diagram illustrating the electrocautery tip and a stent space portion in accordance with the present disclosure, and FIG. 16 is a side cross-sectional diagram illustrating the state that is induced by a guide wire in the disclosure illustrated in FIG. 15.

First, prior to the description of the present disclosure, referring to FIG. 2, a treatment method by a circuit system provided with a anode-type electrical cautery tip 23 is disclosed. This is for explaining an operation principle of the anode-type electrical cautery tip 23.

In the anode-type electrical cautery tip 23, any one electrode body of the electrocautery tip is connected to an external current source 21 using a conduction wire 22, and the other electrode body is also connected to the external current source 21 using a conduction wire 25.

Thereafter, when the practitioner determines a current value and performs the treatment, the current is immediately conducted and flows between the electrode bodies of the anode-type electrical cautery tip 23 and the cauterization operation of the body tissue is performed.

As a result, a current flow distance in the body is minimized, such that it is possible to alleviate the side effects such as electric shock to the body, tissue burns, or tissue necrosis compared to the electrocautery using a mono pole.

The electrocautery tip in accordance with the present disclosure is based on the basic principle described above. Hereinafter, the present disclosure will be described.

Referring to FIGS. 3 to 16, the stent delivery system 100 in accordance with the present disclosure can be configured to include a connector portion 200, an electrocautery tip 300, a delivery portion 400, and a stent space portion 130.

In FIG. 3, a whole appearance diagram of the stent delivery system 100 in accordance with an embodiment of the present disclosure is illustrated. The electrocautery tip 300 is located on the front end portion of the present disclosure, the delivery portion 400 is located on the middle portion thereof, and although not illustrated, but the stent space portion 130 (referring to FIG. 15) is located adjacent to the electrocautery tip 300 inside the delivery portion 400. Then, the connector portion 200 connected to an external current source 110 is located on the rear end portion thereof.

Referring to FIG. 4, a more detailed structure of the connector portion 200 can be illustrated. The connector portion 200 can include a plurality of connection connectors 210, at least one of which is connected to the external current source 110 at a different pole.

In the embodiment of the present disclosure, the connection connector 210 can be divided into a first connection connector 221 and a second connection connector 231.

A first connection protrusion 223 is located on the end portion of the first connection connector 221 and is connected to any one pole of the external current source 110 by a conduction wire; and the first connector body 221 itself of the first connection connector 221 can be connected to a first electrode line 123 by a method of welding bonding, knotting bonding, etc.

Then, a second connection protrusion 233 is located on the end portion of the second connection connector 231 and is connected to the other one pole of the external current source 110 by a conduction wire; and the second connector body 231 itself of the second connection connector 231 can be connected to a second electrode line 125 by a method of welding bonding, knotting bonding, etc.

Herein, the external current source 110 can be a high frequency generator or a low frequency generator, but is not necessarily limited thereto. In addition, the connector portion 200 can be formed of a conductive metal material in which a current flows smoothly.

The connector portion 200 can be located inside the second handle portion 480. Then, a wire outlet 403 can be located on the end portion of the second handle portion 480.

The current supplied from the external current source 110 flows to the first connector body 221 through the first connection protrusion 223 and flows to the first electrode line 123 connected thereto. Then, the current flows to the second electrode line 125 through a first electrode body 313, a second electrode body 315, and the flow in the body in the anode-type electrical cautery tip 300, and flows the second connector body 231 and the second connection protrusion 233 to circulate to the external current source 110. Of course, the direction of current flow can be reversed.

Next, referring to FIGS. 5 and 6, a structure of one shape of the electrocautery tip 300 in accordance with the present disclosure is disclosed. The electrocautery tip 300 can integrally include a plurality of electrode bodies 310 that are connected to a plurality of electrode lines corresponding to the plurality of connection connectors 210 and at least one of which is conducted to a different pole.

Specifically, the electrocautery tip 300 can be configured to include a tip insulating member 320 having a tip guide hole 321 formed therein, a first electrode body 313 located on one side surface of the tip insulating member 320 and forming any one pole, and a second electrode body 315 located on the other side surface of the tip insulating member 320 and forming the other one pole.

A first connection hole 313a is a portion that is located on the first electrode body 313, and connects the first electrode line 123 by welding bonding, knotting bonding, etc. Then, a second connection hole 315a is a portion that is located on the second electrode body 315, and also connects the second electrode line 125 by welding bonding, knotting bonding, etc.

One side portions of the first electrode body 313 and the second electrode body 315 can be processed in the tapered shape in the direction facing each other so that they can be easily inserted into the body tissue upon electrocautery.

FIG. 6 illustrates the shape of the tip insulating member 320 interposed between the first electrode body 313 and the second electrode body 315. A front wing portion 322 of the tip insulating member 320 is the same tapered shape as the electrode body 310, and a stepped portion 323 is formed on the middle portion thereof so that the electrode body 310 can be stably seated on both surfaces of the tip insulating member 320. Then, a rear wing portion 324 is also processed to be slightly protruded corresponding to the external boundary shape of the electrode body 310.

A connection hole 325 is also formed on the tip insulating member 320 to connect the electrode line by the knot bonding.

The first and second electrode bodies 313, 315 and the tip insulating member 320 can be mutually bonded by a brazing bonding using a filler made of AgCu or copper or silver, or mutually bonded by a heterogeneous material bonding using polymer or mutually bonded by a mechanical fitting.

The brazing bonding method melts only the filler using the filler having the melting temperature lower than those of the first and second electrode bodies 313, 315 without melting the first and second electrode bodies 313, 315 to fill a narrow gap between the first and second electrode bodies 313, 315 and the tip insulating member 320 using spreadability, wettability, capillary phenomenon, etc. to be bonded, such that it is possible to minimize deformation and damage of the product while maintaining proper strength.

FIG. 7 illustrates the direction of a current flow, and the current flowing to the first electrode body 313 along the first electrode line 123 flows in the direction of the second electrode body 315 along the in-body Z. Then, the current flows along the second electrode line 125 connected to the second electrode body 315. In this time, the electrocautery operation is generated in the body area Z.

FIG. 8 illustrates another shape of the electrocautery tip 300 in accordance with the present disclosure. The electrode body 310 can be divided into four parts, and in this case, each of the divided electrode bodies 317a, 317b, 317c, 317d is connected to each of the divided electrode lines 127a, 127b, 127c, 127d.

Accordingly, at least one of the divided electrode bodies can have a different pole from other divided electrode bodies. For example, any one of the divided electrode bodies 317a, 317c has positive poles and other divided electrode bodies 317b, 317d have negative poles. Since the current also flows from the positive pole to the negative pole, the electrocautery operation proceeds.

Preferably, the electrode body 310 will be suitable for having a structure divided by two. However, depending on the treatment environment, a structure divided by four can be adopted, and accordingly, it is not necessarily limited thereto, and other structures such as the structures divided by three, five, etc. can be sufficiently considered depending upon the treatment intention.

Next, in FIGS. 9 and 10, disclosed is a method of connecting the first electrode line 123 and the second electrode line 125 to the first electrode body 313 and the second electrode body 315, respectively.

First, in FIG. 9, disclosed is a structure that connects the first electrode line 123 and the second electrode line 125 by tying them in the first connection hole 313a and the second connection hole 315a in the knotted manner. In this case, it is knotted through the connection hole 325 illustrated in FIG. 6.

Then, in FIG. 10, disclosed is a structure that connects the first electrode line 123 and the second electrode line 125 to the first connection hole 313a and the second connection hole 315a through welding bonding W using resistance welding, laser welding, lead-free solder, etc.

Of course, it is not limited thereto, and the connection method of the electrode line can be also implemented in other forms.

Then, the delivery portion 400 can have one side connected to the electrocautery tip 300 and the other side connected to the connector portion 200. The delivery portion 400 can be configured to include a first internal tube 410, a second internal tube 430, an external tube 450, a first handle portion 470, a second handle portion 480, and a movable bar 490.

Hereinafter, the insulating material used in the present disclosure can be selectively applied or compositely applied from polyurethane, polyester, polyimide, other plastic materials, ceramic, silicone, fluorine resin, teflon, zirconia, sialon, etc. Of course, it is not limited thereto, and other materials can be included of course.

Referring to FIGS. 11 to 15, the first internal tube 410 is a portion that is located at the innermost side in the delivery portion 400, and the first electrode line 123 and the second electrode line 125 connected to the electrocautery tip 300 can be located thereon.

The first internal tube 410 can be divided into three shapes depending upon the location of the electrode line 120.

First, referring to FIG. 11, disclosed is one shape of the first internal tube 410. In this shape, the first internal tube 410 is provided as an insulating coating agent. Then, the first electrode line 123 and the second electrode line 125 are individually insulation-coated, and the first electrode line 123 and the second electrode line 125 are integrally insulation-coated with the first internal tube 410 again and can be located as the electrode line 120a of the straight-line shape along the internal longitudinal direction of the first internal tube 410.

When the plurality of insulation-coatings described above are performed, deterioration damage due to a short circuit between the first electrode line 123 and the second electrode line 125 can be prevented.

Of course, when located in the straight-line shape, the individual insulation-coating of the first electrode line 123 and the second electrode line 125 can be omitted. However, when located in the spiral shape or the woven shape that will be described below, the insulation-coating for each electrode line should be performed.

A more detailed location structure can be a structure in which the first electrode line 123 and the second electrode line 125 are located to face each other in parallel along the outside longitudinal direction of the first internal tube 410 that is an insulation-coating agent, and the internal tube 410, the first electrode line 123, and the second electrode line 125 are again insulation-coated all together on the outer portion thereof.

As another example, the first internal tube 410 has an inner hole 411 formed at the inner central side thereof, and for this purpose, should have a constant thickness; and the first electrode line 123 and the second electrode line 125 can be a structure that is located on the thickness portion to be insulated together.

Of course, it is not necessarily limited to the above structure, and other structures that can maintain the insulating property are also applicable.

In this time, the first internal tube 410 can be located through the inside of the movable bar 490. Then, after passing through the movable bar 490, as described above, the first electrode line 123 is connected to the first connection connector 220, and the second electrode line 125 is connected to the second connection connector 230.

A portion that is in contact with the electrocautery tip 300 of the end portions of the first electrode line 123 and the second electrode line 125 can be weld-bonded W to be fused and electrically connected thereto, as illustrated in FIG. 15, and of course, it is not limited to the connection method, and the knotting method is also applicable.

Meanwhile, the movable bar 490 can be implemented as a conductive material such as a metal material and can be formed with a stepped portion with a diameter slightly reduced along the outside circumference of the portion that is exposed between the first handle portion 470 and the second handle portion 480 in a part of the movable bar 490; and an insulating material such as a bar insulation body 493 can be deposited on the stepped portion in order to prevent the electric shock to the practitioner.

The bar insulation body 493 can be a PTFE (polytetrafluoroethylene) coating agent. It is excellent in chemical resistance, heat resistance, etc. and can be suitable as an insulating material for a medical device using electricity.

Of course, it is not necessarily limited to the above structure, and other structures that can maintain the insulating property are also applicable.

Then, referring to FIG. 12, another shape of the first internal tube 410 is disclosed. In this shape, the first internal tube 410 is provided as an insulating coating agent, and the first electrode line 123 and the second electrode line 125 are individually insulation-coated, respectively. Then, the first electrode line 123 and the second electrode line 125 can be coated integrally with the first internal tube 410 once again and can be located as the electrode line 120b wound in the spiral direction along the circumference of the first internal tube 410.

In this time, the first electrode line 123 and the second electrode line 125 can be implemented as a conductive metal material, and the first electrode line 123 and the second electrode line 125 are located on the first internal tube 410 while wound in plural, such that the rigidity of the first internal tube 410 is enhanced.

Preferably, an inner hole 411 is formed at an internal central side of the first internal tube 410, and for this purpose, the first internal tube 410 has a constant thickness. The first electrode line 123 and the second electrode line 125 are individually insulated and located on the thickness portion, and accordingly, the first electrode line 123 and the second electrode line 125 are entirely surrounded by an insulating coating agent to be located along the circumference of the first internal tube 410 while wound in plural in the spiral direction thereof.

Since each of the first electrode line 123 and the second electrode line 125 is individually coated, the possibility of a short circuit is reduced. Deterioration damage of the first internal tube 410 due to the above can be prevented.

Then, referring to FIG. 13, another form of the first internal tube 410 is disclosed. In this shape, the first internal tube 410 is provided as an insulating coating agent, and the first electrode line 123 and the second electrode line 125 are individually insulation-coated. Then, the first electrode line 123 and the second electrode line 125 are coated integrally with the first internal tube 410 once again and are located as the electrode line 120c of the woven shape along the circumference of the first internal tube 410.

In this time, the electrode line 120c can be formed of a metal material, and the electrode line 120c is repeatedly located on the first internal tube 410 in the woven shape, such that the rigidity of the first internal tube 410 is enhanced.

Accurately, the inner hole 411 is formed at the internal central side of the first internal tube 410, and for this purpose, the first internal tube 410 has a constant thickness. The first electrode line 123 and the second electrode line 125 are located on the thickness portion and accordingly, the electrode line 120c is entirely surrounded by the insulating coating agent to be located along the circumference of the first internal tube 410 in the repeatedly woven shape.

Of course, since the first electrode line 123 and the second electrode line 125 are individually insulated, a short circuit between the first electrode line 123 and the second electrode line 125 can be blocked.

As described above, the present disclosure can achieve the additional effects in that not only the current can be conducted but also the rigidity of the first internal tube 410 can be enhanced through the structure of the spiral-shaped electrode line 120b and the woven-shaped electrode line 120c in the first internal tube 410. Of course, it is not limited to the spiral shape and the woven shape, and other structures for rigidity enhancement are also applicable.

Next, referring to FIGS. 11 and 15, the second internal tube 430 is located to surround a part of the outside circumference of the first internal tube 410, and can be provided to be connected with the first internal tube 410 to be integrally moved. The second internal tube 430 can be implemented as an insulating material.

Referring to FIG. 15, the second internal tube 430 is located to surround a part of the outside circumference of the first internal tube 410, and in this time, it can be confirmed that a sign block 433 pushing the stent 150 is located on the end portion of the second internal tube 430.

Then, referring to FIG. 11, it can be confirmed that the second internal tube 430 is located inside the external tube 450 and is fitted into and connected to the outside circumference of a tube connection portion 492 of the movable bar 490; and it can be confirmed that the first internal tube 410 located therein is fitted into and connected to a through-hole of the tube connection portion 492 of the movable bar 490.

Accordingly, when the practitioner moves the movable bar 490, the first internal tube 410 and the second internal tube 430 connected to the movable bar 490 are integrally moved together in the movement direction of the movable bar 490.

Next, referring to FIGS. 11 and 15, the external tube 450 can be a portion that is located to surround the second internal tube 430 and is fixedly connected to the end portion of the first handle portion 470. That is, since the external tube 450 is fixed to the first handle portion 470, it does not move upon the movement of the movable bar 490, but guides and supports the movement of the first internal tube 410 and the second internal tube 430. The external tube 450 can be implemented as an insulating material.

Referring to FIG. 15, it can be seen that the stent 150 is located on the stent space portion 130 formed by the first internal tube 410 and the external tube 450 in the non-extended state. That is, the stent 150 is located along the circumference of the portion that is surrounded by the second internal tube 430 in the first internal tube 410 to be not supported, and the stent 150 maintains the non-extended state while being in contact with the inner circumferential surface of the external tube 450.

In this time, a stent support block 131 can be located on the outer circumferential surface of the first internal tube 410.

Then, referring to FIG. 11, the first handle portion 470 is a portion connected to the end portion of the external tube 450, and can be a portion provided for the practitioner to grab in order to move the movable bar 490.

A fixing handle 473 can be located on one side portion of the first handle portion 470. When the practitioner wants to restrict the movement of the movable bar 490 after moving the movable bar 490, the practitioner can rotate the fixing handle 473 in one direction. Although not illustrated in the drawing, when the fixing handle 473 is rotated in one direction, the movable bar 490 is pressed to restrict the movement of the movable bar 490. Conversely, when the practitioner wants to move the movable bar 490 again, the practitioner can rotate the fixing handle 473 in the opposite direction to loosen the pressure on the movable bar 490.

The fixing handle 473 is provided to locate the stent 150 at the accurate body tissue area when being adjacent to the body tissue area where the stent 150 should be expanded. This is because when the movable bar 490 moves during the treatment, the location of the stent 150 can be inaccurately located.

Meanwhile, referring to FIG. 14, another form for fixing the movable bar 490 is disclosed in the present disclosure. The delivery portion 400 can be configured to further include a movement adjustment portion 475 for adjusting the movement of a first grip body 471 moving along the movable bar 490 in the stepwise manner Conversely, this can adjust the movement of the movable bar 490 in the stepwise manner through the relation with the first grip body 471.

The movement adjustment unit 475 can be configured to include an uneven portion 476 and a fixing portion 477.

First, the uneven portion 476 can be formed in plural with a plurality of bending shapes along the longitudinal direction of the movable bar 490. Then, the fixing portion 477 can be located inside the first handle portion 470 in order to fix the movement of the first grip body 471 moving along the movable bar 490 while being coupled to the uneven portion 476.

Specifically, the fixing portion 477 can be also configured to include an elastic body 478 and a fixing block 479. The elastic body 478 can be located on an internal space formed inside the fixing handle 473 included in the first handle portion 470. Of course, it can be another location on the first handle portion 470. The elastic body 478 can be the shape such as a coil spring and a plate spring, but it is not limited thereto as long as it can provide an elastic force.

Then, the fixing block 479 can be implemented as the shape that has one side tightly closed to the elastic body 478 and the other side protruded toward the first inner hole 472. In this time, when the practitioner pulls or pushes the movable bar 490, a rolling wheel 479a can be located on the fixing block 479 in order to relatively, easily go beyond the bent shape of the uneven portion 476.

The stepwise movement of the movable bar 490 through the above-described structure enables the stable stepwise self-expansion of the stent in the treatment area of the body tissue when the actual practitioner performs the stent treatment.

The completeness of the stent treatment can change depending on the treatment environment, the skill of the practitioner, etc. When the practitioner is immature so forcibly pulls the movable bar 490 or shakes the movable bar 490 upon the pulling, the vibration can be delivered to the stent and thereby, the self-expansion of the stent is not performed smoothly.

In this time, if the movable bar 490 can be moved in the stepwise manner and fixed, the movement of the external tube 450 by the pulling of the movable bar 490 can be clearly adjusted in the stepwise manner as well, such that the exposure of the stent is also slowly proceeded in the stepwise manner. This induces the accurate self-expanding of the stent and also enhances the treatment effect. The carelessness of the practitioner can be mitigated a little more or prevented.

Next, referring to FIGS. 15 and 16, a side cross-sectional diagram of the electrocautery tip 300 is disclosed.

The tip insulating member 320 has a tip guide hole 321, on which the guide wire 140 is inserted and located, formed at the central side thereof. Then, both surfaces of the tip insulating member 320 are formed with the first electrode body 313 and the second electrode body 315, and weld-bonded and connected with the first electrode line 123 and the second electrode line 125, respectively. Of course, the knotting method is also applicable.

In addition, a part of the outer circumferential surface of the electrode body 310 can be insulation-coated by an external insulating body 380 by the molding method. This is to prevent current from flowing to the area other than the tissue to be cauterized in the body area.

The electrode body 310 can be entirely a circular cross-sectional shape, and the electrode body 310 can be a portion that forms a hole by applying a current to heat the body tissue, and can be a conductive material such as a metal material. For example, it can be a metal material such as stainless and Ni+Ti alloy.

Then, in an embodiment of the present disclosure, an end portion 380a of the external insulating body 380 can be molded in the tapered shape, and the structure helps to relatively perform easily the removal operation when the stent 150 is delivered to the body tissue and then the electrocautery tip 300 is pulled out.

That is, a part of the external insulating body 380 can be implemented in the shape tapered in the direction opposite to the one side portions of the first and second electrode bodies 313, 315, and this is to pull it out more smoothly when the electrocautery tip 300 is pulled out from the body.

The body tissue is mainly made of protein, and even if a cauterization hole is formed by the electrocautery tip 300, there is a property that the cauterization hole becomes narrow due to the flexibility of the body tissue.

In this time, if the external insulating body 380 is tapered in the direction opposite to the electrode body 310, the cauterization hole is widened while spreading along the tapered shape when the practitioner pulls out the electrocautery tip 300 through the cauterization hole, such that the electrocautery tip 300 is easily removed.

In this case, the first internal tube 410 is inserted into the external insulating body 380 and adhered to the electrode body 310.

Of course, the external insulating body 380 is not necessarily limited to the above shapes.

Meanwhile, FIG. 17 is a diagram illustrating a structure of a coupling portion formed on the electrocautery tip in accordance with the present disclosure, FIG. 18 is a diagram illustrating the state in which a variable ring is mounted in the disclosure illustrated in FIG. 17, FIG. 19 is a side cross-sectional diagram illustrating one shape of the variable ring, FIG. 20 is a side cross-sectional diagram illustrating another shape of the variable ring, FIGS. 21 to 25 are diagrams illustrating various shapes of an electrocautery protrusion in accordance with the present disclosure, and FIGS. 26 and 27 are diagrams illustrating various shapes of the variable ring having different lengths.

First, referring to FIGS. 17 to 20, as another embodiment of the electrocautery tip 300, it can further include a coupling portion 330 and a variable ring 350.

The coupling portion 330 can be located on parts of the outer circumferential surfaces of the electrode body 310 and the tip insulating member 320. In the embodiment of the present disclosure, the coupling portion 330 can be provided in the thread shape, but is a portion that is in contact with the body tissue, such that the protrusion portion of the thread can be processed to be smoothly rounded in order to prevent fine damage of the body tissue.

The thread can be processed in the same manner not only on the electrode body 310 but also on the tip insulating member 320.

As illustrated in FIGS. 19 and 20, the variable ring 350 can be a portion connected to the coupling portion 330 in order to change the diameter of the electrode body 310. The variable ring 350 can be a circular ring shape, a thread corresponding to the thread of the coupling portion 330 can be processed on the inner circumferential surface thereof, and can be also provided to be rounding-processed smoothly.

Referring to FIG. 18, a first ring portion 351 of the variable ring 350 can be made of the same material as the electrode body 310, that is, it can be a conductive metal material. The first ring portion 351 of the variable ring 350 also functions to puncture the body tissue.

Then, in order to exert the characteristics of the anode-type electrical cautery tip 300, a second ring portion 353 of the variable ring 350 can be made of the same insulating material as the tip insulating member 320.

As illustrated in FIGS. 18 and 19, an example of the variable ring 350 can be the shape that the outer circumferential surface of the variable ring 350 is rounded. In this case, when heat is applied to the body tissue to puncture therein and the electrode body 310 inserts into the body tissue or comes out after treating the stent 150, it is possible to further smoothly insert into or come out the body tissue without damaging on the body tissue due to the rounded outer circumferential surface thereof. Of course, since the variable ring 350 tightly contacts with the electrode body 310 to be electrically connected thereto, it is also possible to adjust the range of the diameter that punctures the body tissue.

For example, when the practitioner wants to reduce the size of a hole in the body tissue, the electrode ring 310 can be used while the variable ring 350 is separated, and conversely, when the practitioner wants to puncture a little larger area in the body tissue where the stent 150 is delivered, the electrode body 310 can be used while interposing the variable ring 350 therebetween.

In the embodiment of the present disclosure, only one rounded variable ring 350 is disclosed, but the shape rounded on the variable ring 350 can be more various, and of course, other shapes can be included within the range that can be inferred from the present disclosure.

In addition, as illustrated in FIG. 20, as another example of the variable ring 350, the outer circumferential surface of the variable ring 350 can be implemented in the tapered shape. In this time, one side of the outer circumferential surface of the variable ring 350 can be tapered in the same direction as the electrode body 310, and the other side of the outer circumferential surface of the variable ring 350 can be tapered in the same direction as the external insulating body 380.

In this case, when the electrode body 310 inserts into the body tissue or comes out after treating the stent 150, the electrode body 310 is also tapered in the same direction as the external insulating body 380, such that it is possible to prevent it from being caught in the hole formed in the body tissue and causing damage.

Of course, since the external insulating body 380 tightly contacts the electrode body 310 to be electrically connected thereto, it is also possible to adjust the range of the diameter that punctures the body tissue. A detailed description thereof is as described above.

In the embodiment of the present disclosure, although only one tapered variable ring 350 is disclosed, the shape tapered on the variable ring 350 can be various, and of course, other shapes can be included within the range that can be inferred from the present disclosure.

In addition, in the embodiment of the present disclosure, one side of the outer circumferential surface of the variable ring 350 can be tapered at an angle (Φ2) smaller than an angle (Φ1) of the electrode body 310, and the other side of the outer circumferential surface of the variable ring 350 can be tapered at an angle smaller than the external insulating body 380.

Even if the variable ring 350 is mounted on the electrode body 310 through the processing, the size of the hole for cauterizing the body tissue with the heat by the conducted current can be further reduced. Of course, it is possible not only to simply reduce the size of the cauterization hole, but also to expand it conversely. The practitioner can have a plurality of variable rings 350 having a taper angle, and can use by changing and coupling the variable rings 350 depending upon the size of the hole in the body tissue to be cauterized.

Meanwhile, referring to FIGS. 19 and 20, an adhesion pad 360 can be located on at least one side of the coupling portion 330 in order to prevent the gap between the inside circumference of the variable ring 350 and the outside circumference of the electrode body 310.

In the embodiment of the present disclosure, the adhesion pad 360 is located on both sides of the coupling portion 330. As a whole, the adhesion pad 360 can be a ring shape, and can be located to be forcedly fitted along the outer circumferential surface of the electrode body 310. The adhesion pad 360 can be a flexible insulating material slightly protruded outwardly from the coupling portion 330.

Due to the location of the adhesion pad 360, after the practitioner has rotated the variable ring 350 and fitted it into the coupling portion 330, the inner circumferential surface of the variable ring 350 and the outer circumferential surface of the electrode body 310 and the tip insulating member 320 are tightly contacted in order to have no gap therebetween. This is because when the electrode body 310 inserts into or comes out the body tissue, it is possible to prevent the phenomenon that blood, tissue, etc. are flowed into the gap, which is spaced between the variable ring 350, and the electrode body 310 and the tip insulating member 320, and are trapped therein.

That is, since both the first ring portion 351 of the variable ring 350 and the electrode body 310 are made of a metallic material, it is difficult to perform the mechanically perfect fitting and a fine gap occurs. The adhesion pad 360 blocks the gap, and this helps the precision of the human body medical instrument.

Of course, the gap between the second ring portion 353 of the variable ring 350 and the tip insulating member 320 can be better than the gap between the first ring portion 351 and the electrode body 310 due to the characteristics of the insulating material, but the gap can be also blocked by the adhesion pad 360.

Meanwhile, FIG. 21 illustrates a shape that views the electrode body 310 from the front thereof in accordance with the present disclosure.

Then, FIG. 22 illustrates another shape of the electrode body 310, which is a structure that the tip guide hole 321 is eccentrically located.

The electrode body 310 on which the eccentric tip guide hole 321 is formed is not used generally, but can be used depending upon the treatment environment. For example, when the stent delivery system 100 in accordance with the present disclosure has been inserted into a branch point where the blood vessel in the vascular system is divided in plural, by rotating the eccentric tip guide hole 311 toward the blood vessel to locate to look at the blood vessel when it is desired to move the electrode body 310 to the blood vessel in the desired direction, it is possible to more easily move the guide wire 140 into the blood vessel.

Then, in the present disclosure, as illustrated in FIGS. 23 to 25, the electrocautery tip 300 can be configured to further include a cauterization protrusion 370 formed on the outer circumferential surface of the electrode body 310. The cauterization protrusion 370 can be located in plural on the outer circumferential surface of the electrode body 310 at predetermined intervals.

It can be confirmed that in FIG. 23, two cauterization protrusions 370 are located at intervals of 180 degrees, and in FIG. 24, four cauterization protrusions 370 are located at intervals of 90 degrees, respectively; and since this guides the direction of the cauterization incision in advance when cauterizing the body tissue, it can be also expected to minimize body tissue damage. As illustrated in FIG. 25, the cauterization protrusions 370 can be also located in the spiral shape rather than the straight-line shape.

The cauterization protrusions 370 can be located at different intervals, respectively, not at predetermined intervals, and other shapes that can be inferred from the present disclosure can be also included in the embodiment of the present disclosure.

In addition, referring to FIGS. 26 and 27, in the embodiment of the present disclosure, the variable rings 350 can be provided to have different thicknesses. For example, first, referring to FIG. 26, when a cauterization hole formed in the body tissue is required in the elliptical shape, the variable ring 350, which is formed so that the thickness D1 of a part of the variable ring 350 is greater than the thickness D2 of other portions thereof, is mounted and used.

When the hole to be cauterized is desired to be protruded on only any one portion, as illustrated in FIG. 27, the variable ring 350, which is formed so that the thickness D3 of any one portion of the variable ring 350 is thicker than the thickness D4 of the other portions thereof, is mounted and used.

It will be apparent that FIGS. 26 and 27 has disclosed two types of the variable rings 350, but the variable ring 350 formed to have various thicknesses that can be inferred within the range having the same purpose can be included therein.

Meanwhile, as another example of the present disclosure, although not illustrated in the drawing, the gap between the plurality of cauterization protrusions 370 can be insulation-coated. In this case, since the electrode body 310 is insulation-coated, the cauterization of the body tissue is performed only for the cauterization protrusion 370, which can reduce the cauterization range of the body tissue. Of course, although not illustrated in the drawing, it can be considered to also perform the insulation-coating for the variable ring 350 depending upon the treatment environment.

An explanation for the structure and various embodiments of the present disclosure is as described above, and hereinafter, a stent delivery method in accordance with the present disclosure will be described.

FIG. 28 is a diagram illustrating the state in which the stent is expanded, and FIGS. 29 to 34 are diagrams illustrating an operation method in which the present disclosure delivers the stent into the body tissue. The reference numerals necessary for the explanation of the operation state will be described with reference to FIGS. 3 to 16.

First, referring to FIG. 29, the practitioner first inserts the guide wire 140 in order to accurately designate the location inside the body to be treated by the stent 150 and to guide the insertion passage of the stent 150. That is, in FIG. 29, the guide wire 140 is inserted into the body tissues T1, T2 to be treated by the stent 150.

Then, when the guide wire 140 is located on the body tissues T1, T2 and the delivery direction of the stent 150 is set, the practitioner fits the end portion of the guide wire 140 into the tip guide hole 321 of the tip insulating member 320, and accordingly, the guide wire 140 is inserted into the tip guide hole 321 and is located by penetrating the inner hole 411 of the first internal tube 410, the bar inner hole 491 of the movable bar 490, and the second inner hole 482 formed inside the second handle portion 480.

Thereafter, as illustrated in FIG. 30, the practitioner grabs the entire stent delivery system 100 and pushes it toward the guide wire 140. As a result, the external tube 450 and the electrocautery tip 300 are inserted into the body tissues T1, T2.

In this time, the connector portion 200 receives a current from the external current source 110, and the first electrode line 123 is connected to the anode of the external current source 110 (for convenience of explanation, assuming that the first electrode line is connected to the positive pole) to flow a current, and the first electrode body 313 connected to the first electrode line 123 has a positive pole.

Then, the second electrode line 125 is connected to the cathode of the external current source 110 (for convenience of explanation, assuming that the second electrode line is connected to the negative pole), and the second electrode body 315 connected to the second electrode line 125 has a negative pole.

Accordingly, as illustrated in the enlarged diagram of FIG. 30, a current E flowing in the first electrode body 313 upon the electrocautery is flowed into the body tissue T1 to flow to the second electrode body 315 at the shortest distance.

In this procedure, in the adhesion portion TB of the body tissue in the path where the current E passes, the electrocautery operation due to the heating reaction occurs and a hole is formed.

The electrocautery operation identically proceeds in the other body tissue T2 as well, and after completing the generation of the hole, as illustrated in FIG. 31, the external tube 450 can be stably inserted into the body tissues T1, T2.

Thereafter, the practitioner pulls out the guide wire 140 through the wire outlet 403 located on the rear end portion of the second inner hole 482 to remove the guide wire 140 from the areas of body tissues T1, T2 and the inside of the stent delivery system 100.

Now, when locating the stent 150 relatively adjacent to the treatment area, the practitioner grabs the first grip portion 470 and the second grip portion 480, and pulls the first handle portion 470 toward the second handle portion 480. In this time, since the first handle portion 470 is connected to the external tube 450 and the second handle portion 480 is connected to the second internal tube 430 by the movable bar 490, the external tube 450 retreats while the first handle portion 470 moves along the movable bar 490.

Herein, since the end portion of the second internal tube 430 and the end portion of the first internal tube 410 are connected to each other, the first internal tube 410 that is in place is exposed to the outside of the external tube 450 as the external tube 450 retreats.

Referring to FIGS. 28 and 32, the stent 150 that has been located in the stent space portion 130 is exposed to the inside of the body tissues T1, T2 as the first internal tube 410 is exposed to the outside of the external tube 450. The stent 150 is unfolded through the self-expansion, and performs its function at the desired areas T1, T2 of the body tissue.

FIGS. 29 to 34 illustrate the state in which the stent 150 is unfolded for the purpose of connecting the two areas T1, T2 of the body tissue, but the present disclosure can be also used for expanding the circulatory system tube such as blood vessel, urethra, and lung in the circulatory system such as blood vessel, urethra, and lung that are contracted or blocked. In addition, the stent 150 can be appropriately used for other body tissues needed.

Referring back to FIG. 32, as the external tube 450 retreats, the stent 150 is relatively pushed back by the sign block 433 located on the end portion of the second internal tube 430. That is, one end portion of the stent 150 is blocked and fixed by the sign block 433, and in this time, the external tube 450 moves backwards, such that it is opened from the other end portion of the stent 150 to the outside of the external tube 450. Then, the stent 150 is located inside the body tissues T1, T2 and is self-expanded slowly.

Herein, the practitioner can confirm the current location of the stent inside the body tissue through the location identification of the sign block 433. For this purpose, the sign block 433 can be painted in a color that the practitioner can identify.

Thereafter, as illustrated in FIG. 33, the practitioner accurately locates the stent 150 in the desired body tissue by slightly pulling the stent 150 that is partially expanded, and then further retreats the first handle portion 470 along the movable bar 490, such that the entire stent 150 is completely self-expanded.

Then, as illustrated in FIG. 34, the stent treatment is completed by slowly pulling out the entire stent delivery system 100 and removing it from the body tissue.

The above description is merely a specific embodiment of the stent delivery system.

It should be understood by those skilled in the art that various substitutions and modifications of the present disclosure can be made in various forms without departing from the spirit and scope of the disclosure as defined in the following claims

INDUSTRIAL APPLICABILITY

The present disclosure relates to a stent delivery system, and more particularly, to a stent delivery system, which minimizes the current flow distance inside the body by integrally conducting two poles to the electrocautery tip, thus enhancing the treatment stability.

The invention claimed is:

1. An apparatus for stent delivery, comprising:
a connector portion configured to be electrically connected to an external current source;
an electrocautery tip having a plurality of electrode bodies connected to a plurality of electrode lines extending from the connector portion;
a delivery portion connected to the electrocautery tip and the connector portion, and accommodating therein the plurality of electrode lines for electrically connecting the electrocautery tip with the connector portion; and
a stent space portion located adjacent to the electrocautery tip inside the delivery portion,
wherein the electrocautery tip includes a tip insulating member having a tip guide hole formed therein,
wherein the tip insulating member includes a plurality of wing portions protruding from an outside surface thereof and extending in a longitudinal direction, the plurality of wing portions respectively having a constant circumferential width, and the plurality of electrode bodies are seated on the outside surface of the tip insulating member between the plurality of wing portions, such that external surfaces of the plurality of wing portions are continuous from those of the plurality of electrode bodies, and
wherein each of the plurality of wing portions includes a front wing portion extending from a proximal end of the tip insulating member to have a tapered surface and a rear wing portion extending from a distal end of the front wing portion to have a non-tapered surface, a radial height of the tapered surface of the front wing portion being higher than that of the non-tapered surface of the rear wing portion at a connection portion between the front wing portion and the rear wing portion.

2. The apparatus for stent delivery according to claim 1, wherein the plurality of electrode bodies comprises:
a first electrode body located on one side surface of the tip insulating member and forming one pole; and
a second electrode body located on another side surface of the tip insulating member and forming another pole.

3. The apparatus for stent delivery according to claim 2, wherein the connector portion includes a first connection connector and a second connection connector, and
wherein the plurality of electrode lines include a first electrode line connecting the first electrode body with the first connection connector, and a second electrode line connecting the second electrode body with the second connection connector.

4. The apparatus for stent delivery according to claim 3, wherein the delivery portion comprises:
a first internal tube having an inner hole formed therein;
a second internal tube disposed to surround at least a part of the first internal tube, and connected to the first internal tube to be integrally moved; and
an external tube disposed to surround at least a part of the second internal tube.

5. The apparatus for stent delivery according to claim 4, wherein the first electrode line and the second electrode line are individually insulation-coated and are arranged on the first internal tube along a longitudinal direction of the first internal tube.

6. The apparatus for stent delivery according to claim 4, wherein the first electrode line and the second electrode line are individually insulation-coated and are arranged to be wound in the spiral direction along a circumference of the first internal tube.

7. The apparatus for stent delivery according to claim 4, wherein the first electrode line and the second electrode line are individually insulation-coated and are arranged to form a woven shape along a circumference of the first internal tube.

8. The apparatus for stent delivery according to claim 4, further comprising a guide wire configured to be disposed in the inner hole of the first internal tube for guiding a movement of the electrocautery tip.

9. The apparatus for stent delivery according to claim 2, wherein the tip guide hole is eccentrically located inside the tip insulating member.

10. The apparatus for stent delivery according to claim 2, wherein the first and second electrode bodies and the tip insulating member are mutually bonded by a brazing bonding using a filler that is made of AgCu or copper or silver, or mutually bonded by a heterogeneous material bonding using polymer, or mutually bonded by a mechanical fitting.

11. The apparatus for stent delivery according to claim 3, wherein the electrocautery tip further comprises an external insulating body surrounding the first and second electrode lines and located adjacent to the first and second electrode bodies.

12. The apparatus for stent delivery according to claim 11, wherein a part of the external insulating body is tapered in a direction opposite to that of one of the first and second electrode bodies.

13. An apparatus for stent delivery, comprising:
a connector portion configured to be electrically connected to an external current source;
an electrocautery tip having a plurality of electrode bodies connected to a plurality of electrode lines extending from the connector portion;
a delivery portion connected to the electrocautery tip and the connector portion, and accommodating therein the plurality of electrode lines for electrically connecting the electrocautery tip with the connector portion; and a stent space portion located adjacent to the electrocautery tip inside the delivery portion, wherein the delivery portion comprises:

a first internal tube having an inner hole formed therein;

a second internal tube disposed to surround at least a part of the first internal tube, and connected to the first internal tube to be integrally moved; and an external tube disposed to surround at least a part of the second internal tube;

a first handle portion connected to the external tube; and a second handle portion connected to the second internal tube by a movable bar, wherein the connector portion is disposed on the second handle portion, and the first internal tube is disposed to penetrate the movable bar and the second handle portion.

14. The apparatus for stent delivery according to claim 13, wherein the delivery portion further comprises a movement adjustment unit for adjusting a movement of the movable bar in a stepwise manner, wherein the delivery portion further comprises:

an uneven portion formed along a longitudinal direction of the movable bar; and a fixing portion disposed inside the first handle portion to be coupled to the uneven portion so as to fix the movement of the movable bar in the stepwise manner.

15. The apparatus for stent delivery according to claim 14, wherein the fixing portion comprises:

an elastic body disposed inside the first handle portion; and a fixing block having one side contacted to the elastic body and another side protruded to the movable bar.

16. The apparatus for stent delivery according to claim 15, wherein the fixing portion further comprises a rolling wheel rotatably located on the fixing block.

17. An apparatus for stent delivery, comprising:

a connector portion configured to be electrically connected to an external current source;

an electrocautery tip having a plurality of electrode bodies connected to a plurality of electrode lines extending from the connector portion;

a delivery portion connected to the electrocautery tip and the connector portion, and accommodating therein the plurality of electrode lines for electrically connecting the electrocautery tip with the connector portion; and a stent space portion located adjacent to the electrocautery tip inside the delivery portion, wherein the electrocautery tip comprises:

a coupling portion formed on a part of outside circumferences of the plurality of electrode bodies; and a variable ring configured to be coupled to the coupling portion in order to change a size of an assembly of the plurality of electrode bodies.

18. The apparatus for stent delivery according to claim 17, wherein a part of an outside of the variable ring is tapered in a same direction as those of the plurality of electrode bodies.

19. The apparatus for stent delivery according to claim 18, wherein a part of the outside of the variable ring is tapered at an angle smaller than the plurality of electrode bodies.

20. The apparatus for stent delivery according to claim 17, wherein an outside circumference of the variable ring is rounded.

21. The apparatus for stent delivery according to claim 20, wherein a part of the variable ring has a different thickness.

22. The apparatus for stent delivery according to claim 17, wherein the electrocautery tip further comprises an adhesion pad disposed on at least one side of the coupling portion.

23. The apparatus for stent delivery according to claim 17, wherein the electrocautery tip further comprises an electrocautery protrusion formed on outside surfaces of the plurality of electrode bodies.

24. The apparatus for stent delivery according to claim 23, wherein the electrocautery protrusion includes a plurality of protrusions disposed on respective outside circumferences of the plurality of electrode bodies at predetermined intervals.

25. The apparatus for stent delivery according to claim 24, wherein the electrocautery protrusion has a straight-line shape.

26. The apparatus for stent delivery according to claim 24, wherein the electrocautery protrusion has a curved shape.

* * * * *